US011234780B2

(12) United States Patent
Eyre et al.

(10) Patent No.: US 11,234,780 B2
(45) Date of Patent: Feb. 1, 2022

(54) SYSTEMS AND METHODS FOR KINEMATIC OPTIMIZATION WITH SHARED ROBOTIC DEGREES-OF-FREEDOM

(71) Applicant: Auris Health, Inc., Redwood City, CA (US)

(72) Inventors: Nicholas J. Eyre, Redwood City, CA (US); Sean Patrick Kelly, San Francisco, CA (US); Sven Wehrmann, Redwood City, CA (US); Yoichiro Dan, Los Altos, CA (US); Travis C. Covington, Campbell, CA (US); Yanan Huang, Sunnyvale, CA (US); David Stephen Mintz, Los Altos Hills, CA (US)

(73) Assignee: Auris Health, Inc., Redwood City, CA (US)

(*) Notice: Subject to any disclaimer, the term of this patent is extended or adjusted under 35 U.S.C. 154(b) by 0 days.

(21) Appl. No.: 17/010,586

(22) Filed: Sep. 2, 2020

(65) Prior Publication Data
US 2021/0068909 A1 Mar. 11, 2021

Related U.S. Application Data

(60) Provisional application No. 62/898,472, filed on Sep. 10, 2019.

(51) Int. Cl.
*G05B 19/04* (2006.01)
*A61B 34/35* (2016.01)
(Continued)

(52) U.S. Cl.
CPC .............. *A61B 34/35* (2016.02); *A61B 34/30* (2016.02); *B25J 9/06* (2013.01); *B25J 9/1643* (2013.01);
(Continued)

(58) Field of Classification Search
CPC .............. A61B 34/35; A61B 2034/301; A61B 2034/302; A61B 2034/305;
(Continued)

(56) References Cited

U.S. PATENT DOCUMENTS 5,199,417 A 4/1993 Muller et al.
5,876,325 A 3/1999 Mizuno et al.
(Continued)

FOREIGN PATENT DOCUMENTS

| EP | 0 347 098 | 2/1996 |
| WO | WO 06/124390 | 11/2006 |
| WO | WO 17/048194 | 3/2017 |

OTHER PUBLICATIONS

Aghakhani et al., May 6, 2013, Task control with remote center of motion constraint for minimally invasive robotic surgery, 2013 IEEE International Conference on Robotics and Automation, pp. 5807-5812.
(Continued)

*Primary Examiner* — Harry Y Oh
(74) *Attorney, Agent, or Firm* — Morgan, Lewis & Bockius LLP

(57) ABSTRACT

Systems and methods for kinematic optimization with shared robotic degrees-of-freedom are provided. In one aspect, a robotic medical system includes a base, an adjustable arm support coupled to the base, and at least one robotic arm coupled to the adjustable arm support. The at least one robotic arm is further configured to be coupled to a medical tool that is configured to be delivered through an incision or natural orifice of a patient. The system further includes a processor configured to adjust a position of the adjustable arm support and the at least one robotic arm while maintaining a remote center of movement of the tool.

20 Claims, 26 Drawing Sheets

(51) Int. Cl.
    *A61B 34/30*     (2016.01)
    *B25J 9/06*      (2006.01)
    *B25J 9/16*      (2006.01)
    *B25J 15/00*     (2006.01)

(52) U.S. Cl.
    CPC ........... *B25J 9/1666* (2013.01); *B25J 9/1689* (2013.01); *B25J 15/0019* (2013.01); *B25J 15/0052* (2013.01); *A61B 2034/301* (2016.02); *A61B 2034/302* (2016.02)

(58) Field of Classification Search
    CPC ... A61B 2090/065; A61B 34/30; A61B 34/37; A61B 34/71; A61B 34/77; A61B 90/361; A61B 90/37; B25J 9/06; B25J 9/1643; B25J 9/1666; B25J 9/1689; B25J 15/0019; B25J 15/0052; B25J 3/00; B25J 9/1682; G05B 2219/39135; G05B 2219/39212; G05B 2219/39322; G05B 2219/40184; G05B 2219/45117
    See application file for complete search history.

(56) References Cited

U.S. PATENT DOCUMENTS

| | | | |
|---|---|---|---|
| 8,021,326 B2 | 9/2011 | Moll et al. | |
| 8,652,030 B2 | 2/2014 | Matsuura et al. | |
| 9,504,604 B2 | 11/2016 | Alvarez | |
| 9,561,083 B2 | 2/2017 | Yu et al. | |
| 9,622,827 B2 | 4/2017 | Yu et al. | |
| 9,636,184 B2 | 5/2017 | Lee et al. | |
| 9,668,768 B2 | 6/2017 | Piron et al. | |
| 9,713,509 B2 | 7/2017 | Schuh et al. | |
| 9,717,563 B2 | 8/2017 | Tognaccini | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,782,229 B2 | 10/2017 | Crawford | |
| 9,788,910 B2 | 10/2017 | Schuh | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,136,959 B2 | 11/2018 | Mintz et al. | |
| 10,145,747 B1 | 12/2018 | Lin et al. | |
| 10,149,720 B2 | 12/2018 | Romo | |
| 10,159,532 B1 | 12/2018 | Ummalaneni et al. | |
| 10,159,533 B2 | 12/2018 | Moll et al. | |
| 10,169,875 B2 | 1/2019 | Mintz et al. | |
| 10,219,874 B2 | 3/2019 | Yu et al. | |
| 10,231,793 B2 | 3/2019 | Romo | |
| 10,231,867 B2 | 3/2019 | Alvarez et al. | |
| 10,244,926 B2 | 4/2019 | Noonan et al. | |
| 10,285,574 B2 | 5/2019 | Landey et al. | |
| 10,299,870 B2 | 5/2019 | Connolly et al. | |
| 10,314,463 B2 | 6/2019 | Agrawal et al. | |
| 10,383,765 B2 | 8/2019 | Alvarez et al. | |
| 10,398,518 B2 | 9/2019 | Yu et al. | |
| 10,405,939 B2 | 9/2019 | Romo et al. | |
| 10,405,940 B2 | 9/2019 | Romo | |
| 10,426,559 B2 | 10/2019 | Graetzel et al. | |
| 10,426,661 B2 | 10/2019 | Kintz | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,493,241 B2 | 12/2019 | Jiang | |
| 10,500,001 B2 | 12/2019 | Yu et al. | |
| 10,517,692 B2 | 12/2019 | Eyre et al. | |
| 10,524,866 B2 | 1/2020 | Srinivasan | |
| 10,539,478 B2 | 1/2020 | Lin | |
| 10,543,048 B2 | 1/2020 | Noonan et al. | |
| 10,555,778 B2 | 2/2020 | Ummalaneni et al. | |
| 10,631,949 B2 | 4/2020 | Schuh et al. | |
| 10,639,108 B2 | 5/2020 | Romo et al. | |
| 10,639,109 B2 | 5/2020 | Bovay et al. | |
| 10,639,114 B2 | 5/2020 | Schuh | |
| 10,646,291 B2 | 5/2020 | Turner | |
| 10,667,871 B2 | 6/2020 | Romo et al. | |
| 10,667,875 B2 | 6/2020 | DeFonzo et al. | |
| 10,682,189 B2 | 6/2020 | Schuh et al. | |
| 10,702,348 B2 | 7/2020 | Moll et al. | |
| 10,716,461 B2 | 7/2020 | Jenkins | |
| 10,743,751 B2 | 8/2020 | Landey et al. | |
| 10,744,035 B2 | 8/2020 | Alvarez et al. | |
| 10,751,140 B2 | 8/2020 | Wallace et al. | |
| 10,765,303 B2 | 9/2020 | Graetzel et al. | |
| 10,765,487 B2 | 9/2020 | Ho | |
| 10,779,898 B2 | 9/2020 | Hill | |
| 10,786,329 B2 | 9/2020 | Schuh et al. | |
| 10,786,432 B2 | 9/2020 | Jornitz et al. | |
| 10,792,464 B2 | 10/2020 | Romo et al. | |
| 10,792,466 B2 | 10/2020 | Landey et al. | |
| 10,813,539 B2 | 10/2020 | Graetzel et al. | |
| 10,814,101 B2 | 10/2020 | Jiang | |
| 10,820,947 B2 | 11/2020 | Julian | |
| 10,820,954 B2 | 11/2020 | Marsot et al. | |
| 10,827,913 B2 | 11/2020 | Ummalaneni et al. | |
| 10,828,118 B2 | 11/2020 | Schuh et al. | |
| 10,835,153 B2 | 11/2020 | Rafii-Tari et al. | |
| 10,850,013 B2 | 12/2020 | Hsu | |
| 2002/0082612 A1 | 6/2002 | Moll et al. | |
| 2003/0181809 A1 | 9/2003 | Hall et al. | |
| 2004/0176751 A1 | 9/2004 | Weitzner et al. | |
| 2006/0058617 A1 | 3/2006 | Sano et al. | |
| 2006/0178556 A1 | 8/2006 | Hasser et al. | |
| 2008/0147089 A1 | 6/2008 | Loh | |
| 2009/0005768 A1 | 1/2009 | Sharareh | |
| 2009/0048611 A1 | 2/2009 | Funda | |
| 2009/0326318 A1 | 12/2009 | Tognaccini | |
| 2010/0100045 A1 | 4/2010 | Pravongviengkham et al. | |
| 2010/0234857 A1 | 9/2010 | Itkowitz | |
| 2010/0286712 A1* | 11/2010 | Won | A61B 34/30 606/130 |
| 2011/0184558 A1* | 7/2011 | Jacob | B25J 9/1643 700/259 |
| 2011/0264112 A1* | 10/2011 | Nowlin | A61B 34/71 606/130 |
| 2011/0277775 A1 | 11/2011 | Holop et al. | |
| 2012/0283747 A1 | 11/2012 | Popovic | |
| 2012/0302869 A1 | 11/2012 | Koyrakh | |
| 2014/0051049 A1 | 2/2014 | Jarc | |
| 2014/0142591 A1 | 5/2014 | Alvarez et al. | |
| 2014/0243801 A1 | 8/2014 | Fanelli et al. | |
| 2014/0357984 A1 | 12/2014 | Wallace et al. | |
| 2015/0025549 A1 | 1/2015 | Kilroy et al. | |
| 2015/0045675 A1 | 2/2015 | Chernomorsky | |
| 2015/0088161 A1 | 3/2015 | Hata | |
| 2015/0223832 A1 | 8/2015 | Swaney | |
| 2015/0297299 A1 | 10/2015 | Yeung | |
| 2015/0305650 A1 | 10/2015 | Hunter | |
| 2016/0157942 A1* | 6/2016 | Gombert | A61B 34/30 606/130 |
| 2016/0270865 A1 | 9/2016 | Landey et al. | |
| 2016/0287279 A1 | 10/2016 | Bovay et al. | |
| 2016/0374771 A1* | 12/2016 | Mirbagheri | A61G 13/02 606/130 |
| 2017/0007337 A1 | 1/2017 | Dan | |
| 2017/0020615 A1* | 1/2017 | Koenig | A61B 46/10 |
| 2017/0071456 A1 | 3/2017 | Ratnakar | |
| 2017/0095299 A1 | 4/2017 | Hendrick | |
| 2017/0135710 A1 | 5/2017 | Hasegawa et al. | |
| 2017/0135833 A1 | 5/2017 | Syed | |

(56) References Cited

U.S. PATENT DOCUMENTS

| | | |
|---|---|---|
| 2017/0143442 A1 | 5/2017 | Tesar |
| 2017/0189118 A1 | 7/2017 | Chopra |
| 2017/0189131 A1 | 7/2017 | Weir |
| 2017/0202627 A1 | 7/2017 | Sramek et al. |
| 2017/0209073 A1 | 7/2017 | Sramek et al. |
| 2017/0290631 A1 | 10/2017 | Lee et al. |
| 2017/0333145 A1* | 11/2017 | Griffiths ............ A61B 34/35 |
| 2018/0025666 A1 | 1/2018 | Ho et al. |
| 2018/0098817 A1 | 4/2018 | Nichogi et al. |
| 2018/0221038 A1 | 8/2018 | Noonan et al. |
| 2018/0221039 A1 | 8/2018 | Shah |
| 2018/0279852 A1 | 10/2018 | Rafii-Tari et al. |
| 2018/0289431 A1 | 10/2018 | Draper et al. |
| 2018/0325499 A1 | 11/2018 | Landey et al. |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0110839 A1 | 4/2019 | Rafii-Tari et al. |
| 2019/0151148 A1 | 5/2019 | Alvarez et al. |
| 2019/0167366 A1 | 6/2019 | Ummalaneni |
| 2019/0175009 A1 | 6/2019 | Mintz |
| 2019/0183585 A1 | 6/2019 | Rafii-Tari et al. |
| 2019/0183587 A1 | 6/2019 | Rafii-Tari et al. |
| 2019/0192244 A1* | 6/2019 | Mirbagheri ............ B25J 9/1689 |
| 2019/0216548 A1 | 7/2019 | Ummalaneni |
| 2019/0216576 A1 | 7/2019 | Eyre |
| 2019/0223974 A1 | 7/2019 | Romo |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298460 A1 | 10/2019 | Al-Jadda |
| 2019/0298465 A1 | 10/2019 | Chin |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0038123 A1 | 2/2020 | Graetzel |
| 2020/0039086 A1 | 2/2020 | Meyer |
| 2020/0046434 A1 | 2/2020 | Graetzel |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100855 A1 | 4/2020 | Leparmentier |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305983 A1 | 10/2020 | Yampolsky |
| 2020/0305989 A1 | 10/2020 | Schuh |
| 2020/0305992 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |
| 2020/0360183 A1 | 11/2020 | Alvarez |
| 2020/0367726 A1 | 11/2020 | Landey et al. |
| 2020/0367981 A1 | 11/2020 | Ho et al. |
| 2020/0375678 A1 | 12/2020 | Wallace |

OTHER PUBLICATIONS

Darwiche, 2015, Operative technique and early experience for robotic assisted laparoscopic nephroureterectomy (RALNU) using da Vinci XI, SpringerPlus, 4:298.

Sasaki, 2017, Laparoscopic hemicolectomy for a patient with situs inversus totalis: a case report, Int. J. Surg. Case Rep. 41:93-96.

* cited by examiner

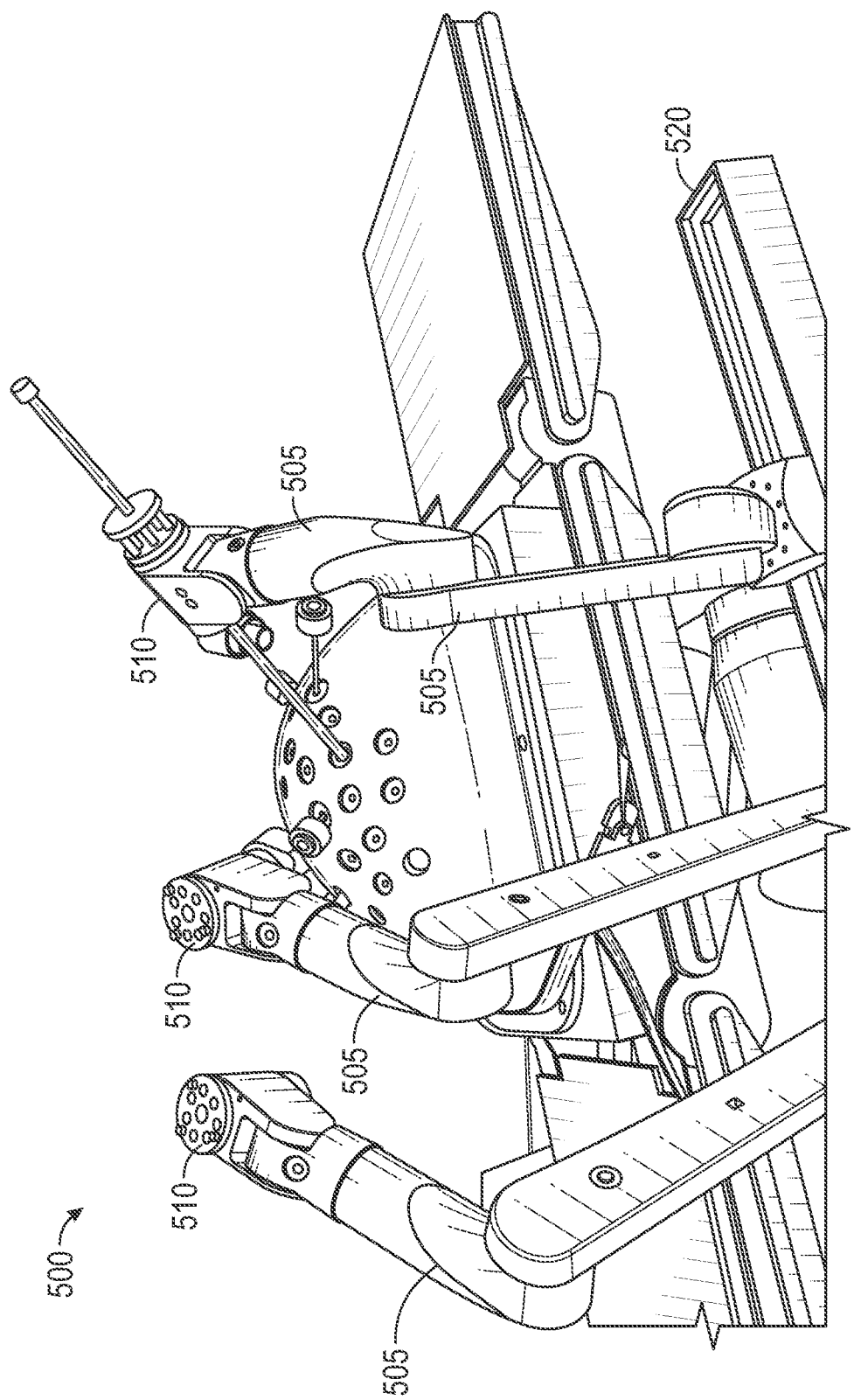

SYSTEMS AND METHODS FOR KINEMATIC OPTIMIZATION WITH SHARED ROBOTIC DEGREES-OF-FREEDOM

CROSS-REFERENCE TO RELATED APPLICATION(S)

This application claims the benefit of U.S. Provisional Application No. 62/898,472, filed Sep. 10, 2019, which is hereby incorporated by reference in its entirety.

TECHNICAL FIELD

The systems and methods disclosed herein are directed to surgical robotics, and more particularly to robotic systems having shared robotic degrees-of-freedom.

BACKGROUND

Medical procedures, such as laparoscopy, may involve accessing and visualizing an internal region of a patient. In a laparoscopic procedure, a medical tool can be inserted into the internal region through a laparoscopic cannula.

In certain procedures, a robotically-enabled medical system may be used to control the insertion and/or manipulation of one or more medical tool(s). The robotically-enabled medical system may a plurality of robotic arms which control the medical tool(s). In positioning the medical tool (s), portions of the robotic arms may move towards another robotic arm or other object in the environment, which can lead to collisions.

SUMMARY

The systems, methods and devices of this disclosure each have several innovative aspects, no single one of which is solely responsible for the desirable attributes disclosed herein.

In one aspect, there is provided robotic medical system, comprising: a base; an adjustable arm support coupled to the base; at least one robotic arm coupled to the adjustable arm support, the at least one robotic arm configured to be coupled to a medical tool that is configured to be delivered through an incision or natural orifice of a patient; and a processor configured to adjust a position of the adjustable arm support and the at least one robotic arm while maintaining a remote center of movement of the tool.

In another aspect, there is provided robotic medical system, comprising: a base; an adjustable arm support coupled to the base; at least a pair of robotic arms coupled to the adjustable arm support, the pair of robotic arms each coupled to a tool that is configured to be delivered through an incision or natural orifice of a patient; and a processor configured to adjust a position of the adjustable arm support and the pair of robotic arms while maintaining a remote center of movement of each of the tools.

In yet another aspect, there is provided a medical method comprising: providing a medical platform comprising an adjustable arm support coupled to a pair of robotic arms, wherein each of the robotic arms is coupled to a medical tool; and adjusting a position of the adjustable arm support and each of the robotic arms coupled thereto while maintaining a remote center of movement of each of the tools.

In still yet another aspect, there is provided a robotic medical system, comprising: a first set of one or more links detachably coupled to a medical tool and configured to perform a first task; and a second set of one or more links configured to perform a second task different from the first task, wherein the first set of one or more links has at least one degree-of-freedom (DoF) and the second set of one or more links has at least one DoF, and wherein the at least one DoF of each of the first set of one or more links and the second set of one or more links are shared to provide null space motion.

In another aspect, there is provided a robotic medical system, comprising: a set of one or more links; and a patient platform configured to support at least a portion of a patient's weight, wherein the set of one or more links has at least one DoF and the patient platform has at least one DoF, and wherein the at least one DoF of each of the set of one or more links and the patient platform are shared to provide null space motion.

In yet another aspect, there is provided a method, comprising: moving a first set of one or more links to perform a first task, wherein the first set of one or more links has at least one DoF; moving a second set of one or more links to perform a second task different from the first task, wherein the second set of one or more links has at least one DoF, wherein the at least one DoF of each of the first set of one or more links and the second set of one or more links are shared; and moving at least one of the first set of one or more links and the second set of one or more links in a null space using the shared at least one DoF.

In still yet another aspect, there is provided a method, comprising: moving a set of one or more links, wherein the first set of one or more links has at least one DoF; moving a patient platform configured to support at least a portion of a patient's weight, wherein the patient platform has at least one DoF, wherein the at least one DoF of each of the set of one or more links and the patient platform are shared; and moving at least one of the set of one or more links and the patient platform in null space using the shared at least one DoF.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 24A and 24B illustrate the movement of two sets of links while maintaining positions of an advanced device manipulator (ADM) and remote center of movement (RCM) in accordance with aspects of this disclosure.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
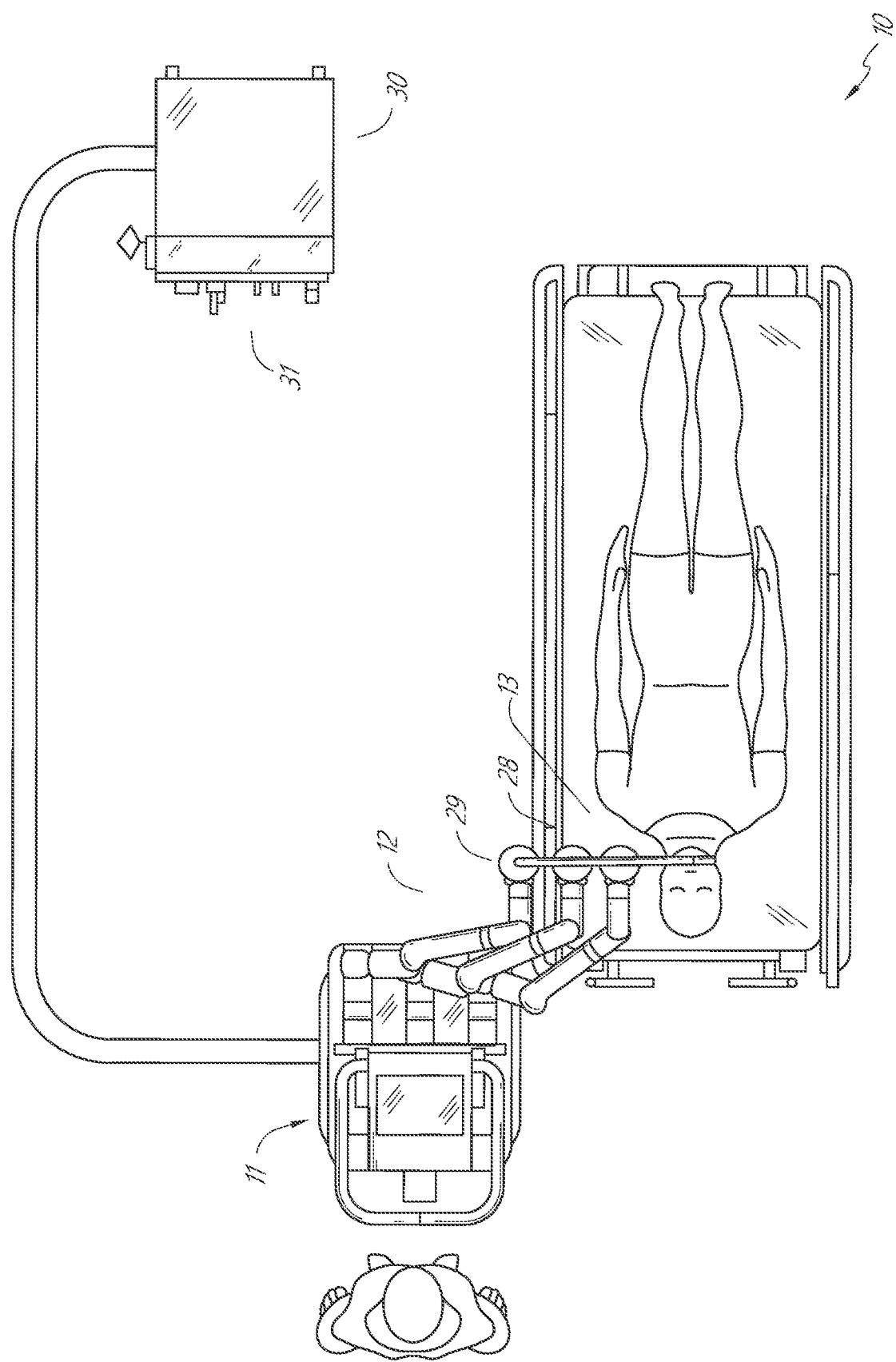
FIG. 1 illustrates an embodiment of a cart-based robotic system arranged for diagnostic and/or therapeutic bronchoscopy.
Figure 2:
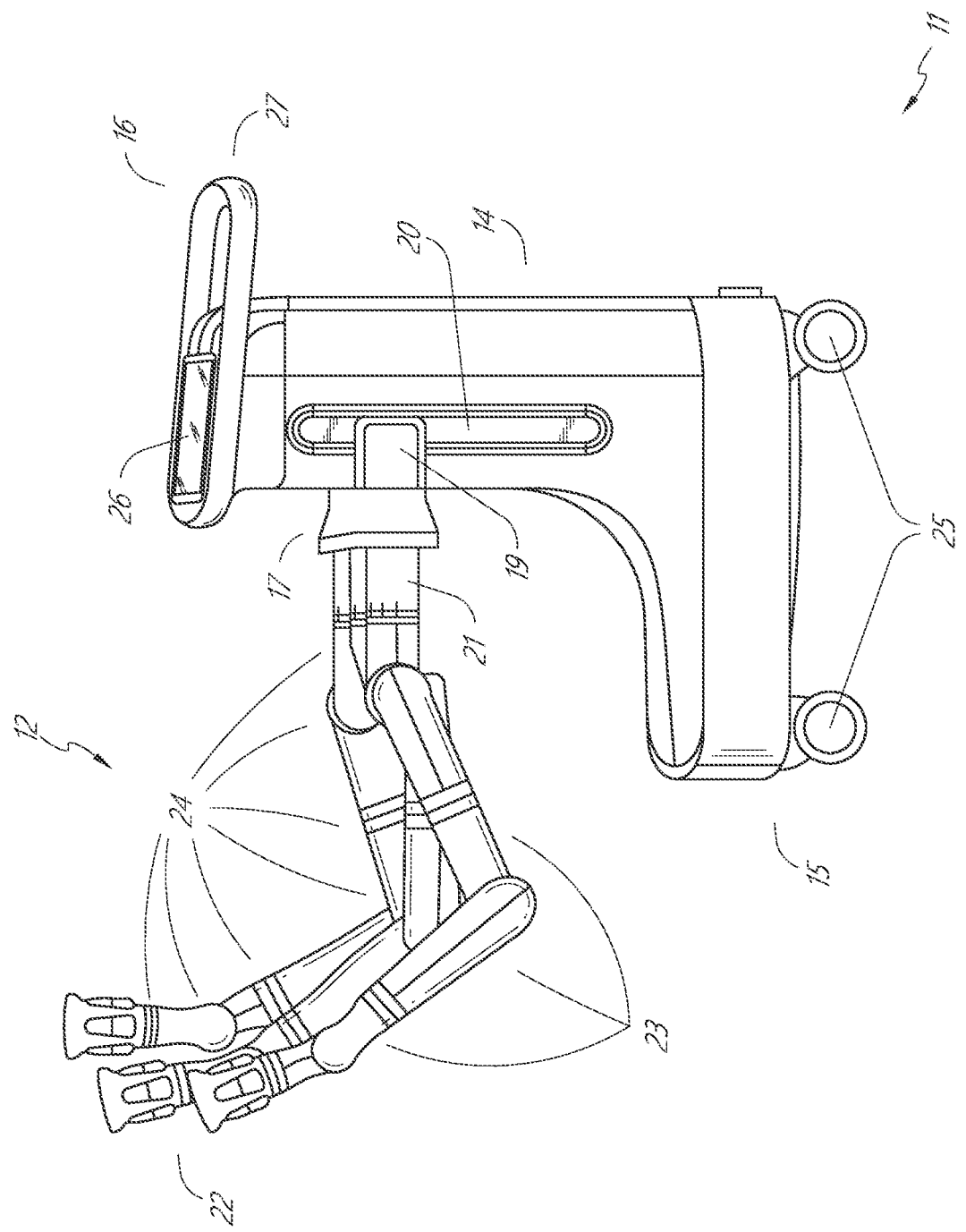
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or repositioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree-of-freedom (DoF) available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
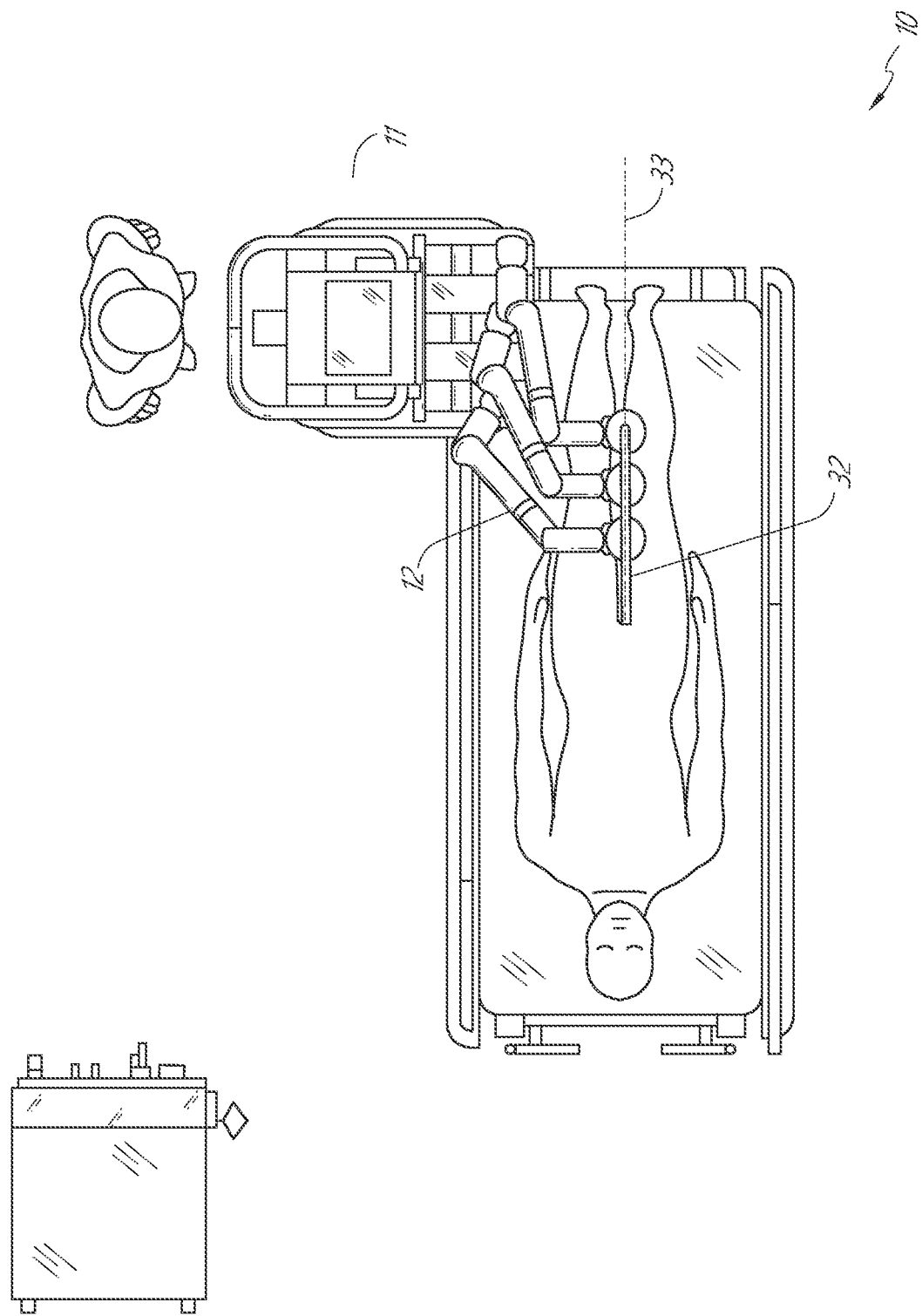
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
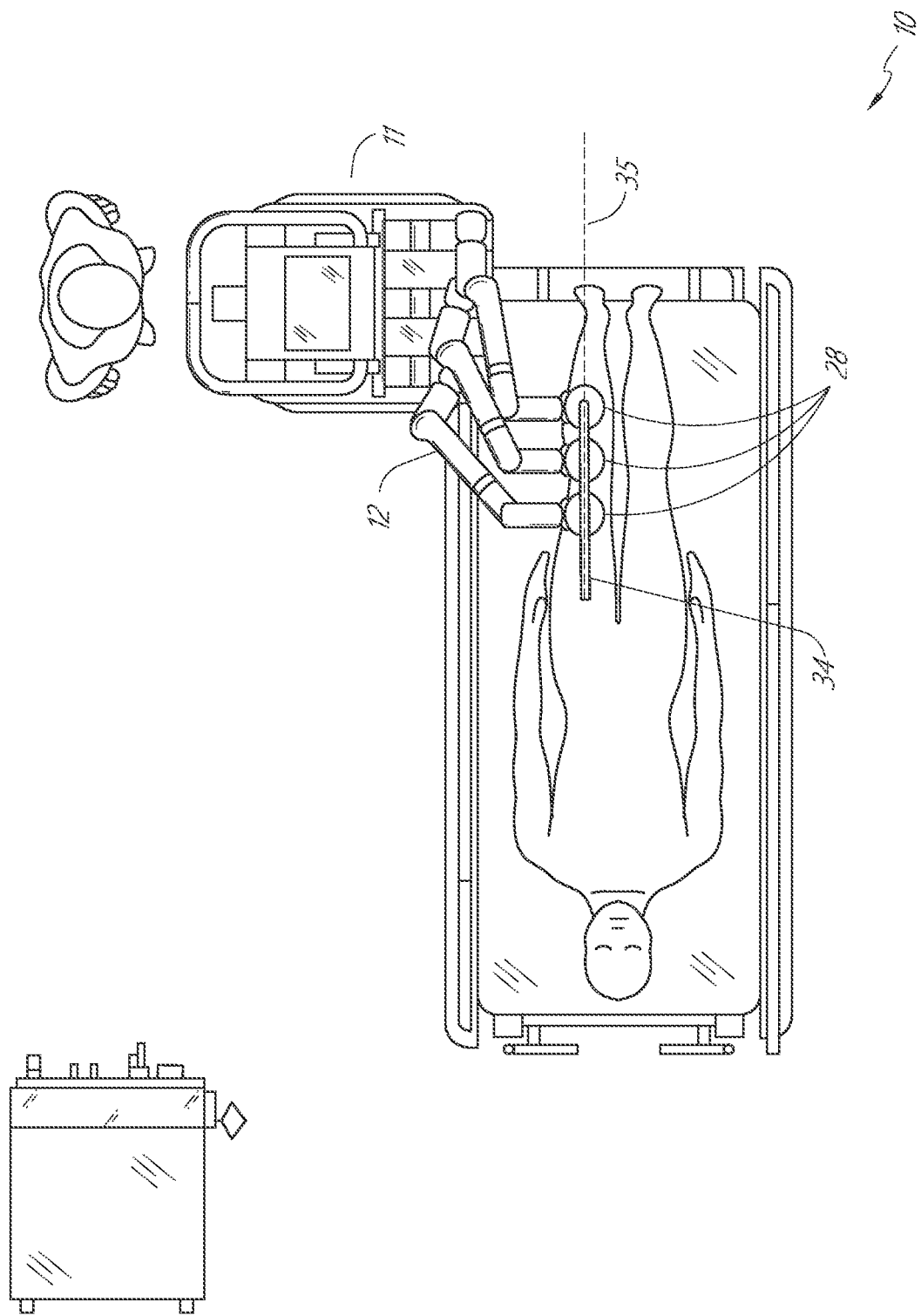
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
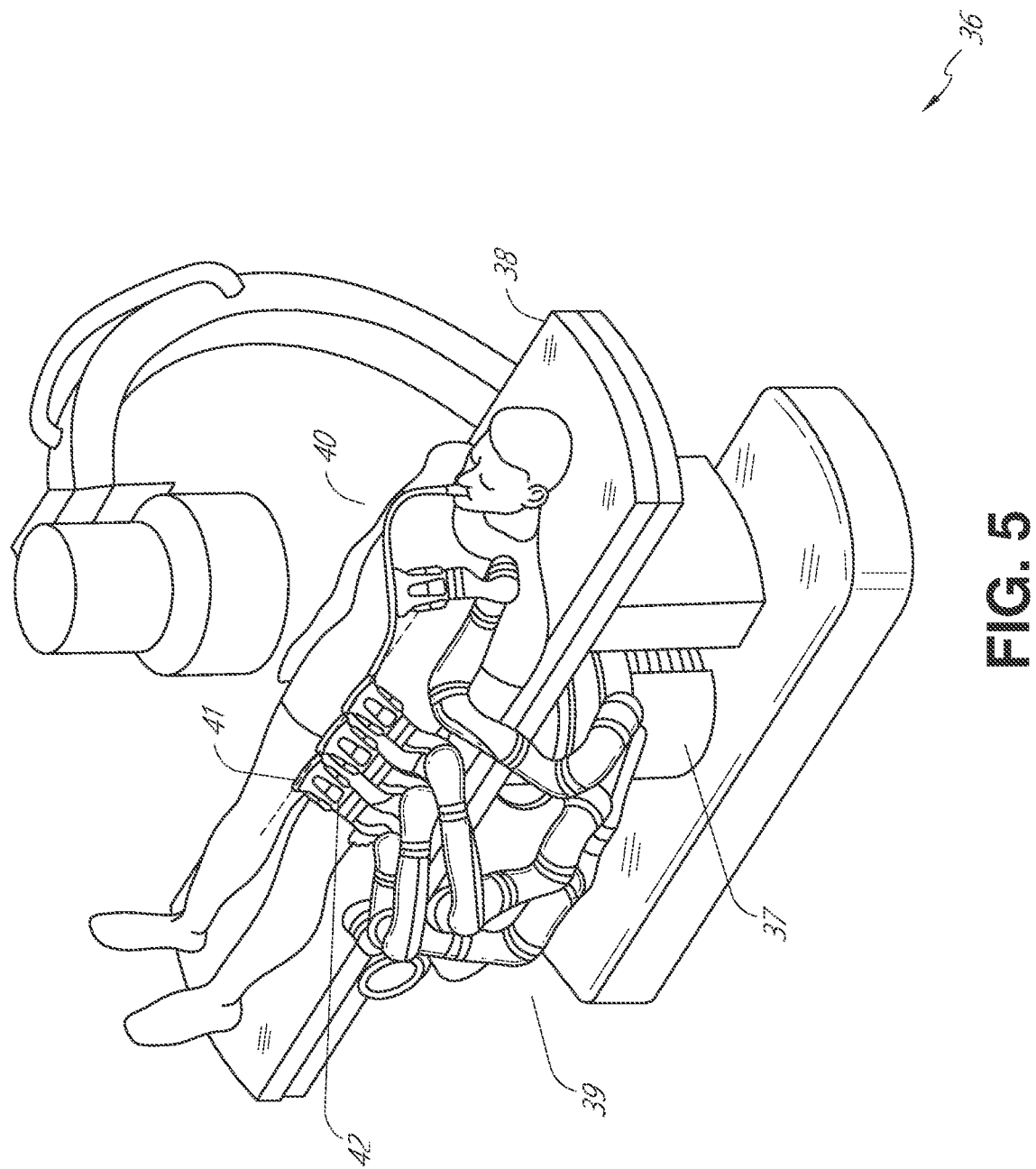
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
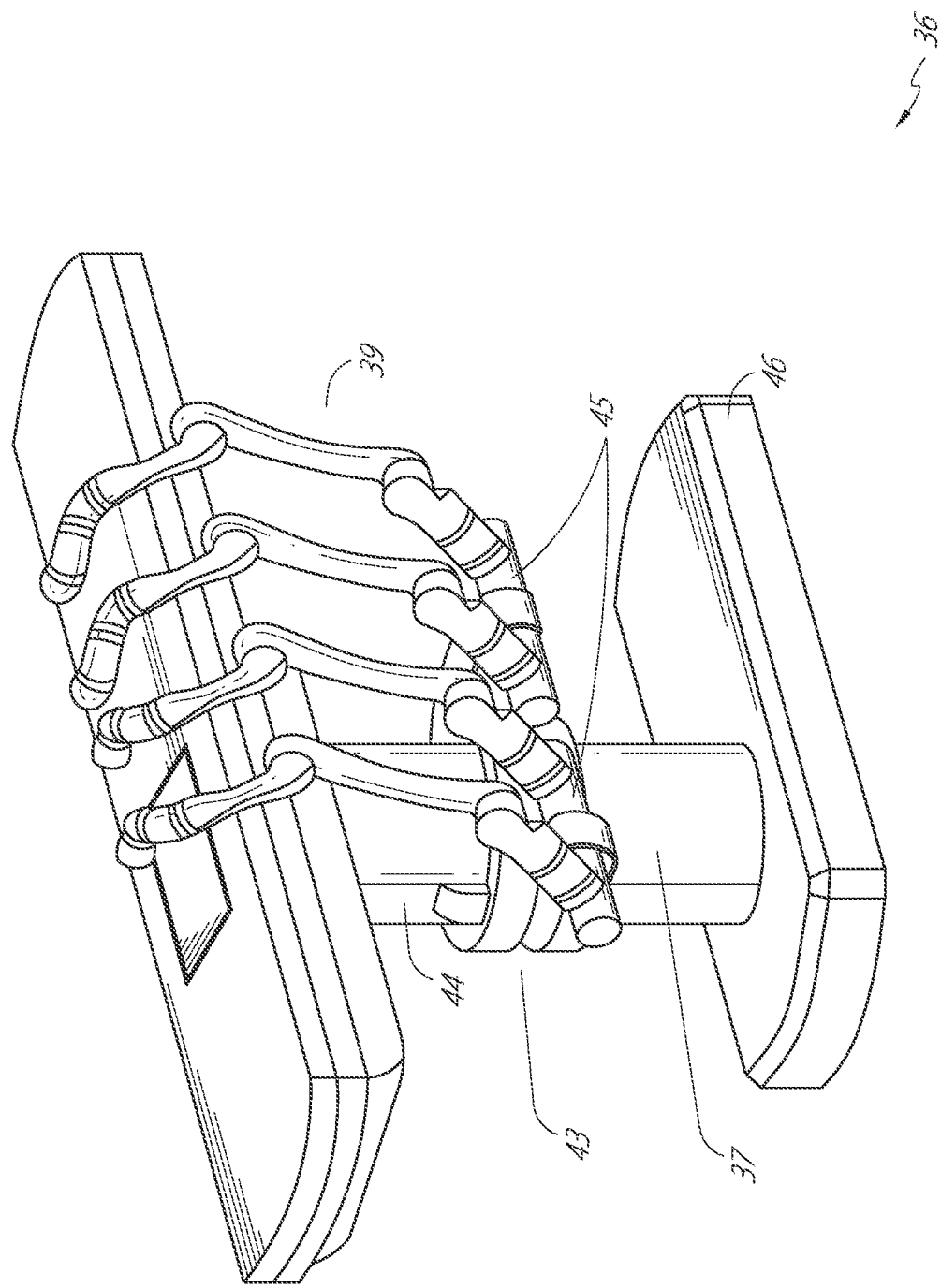
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
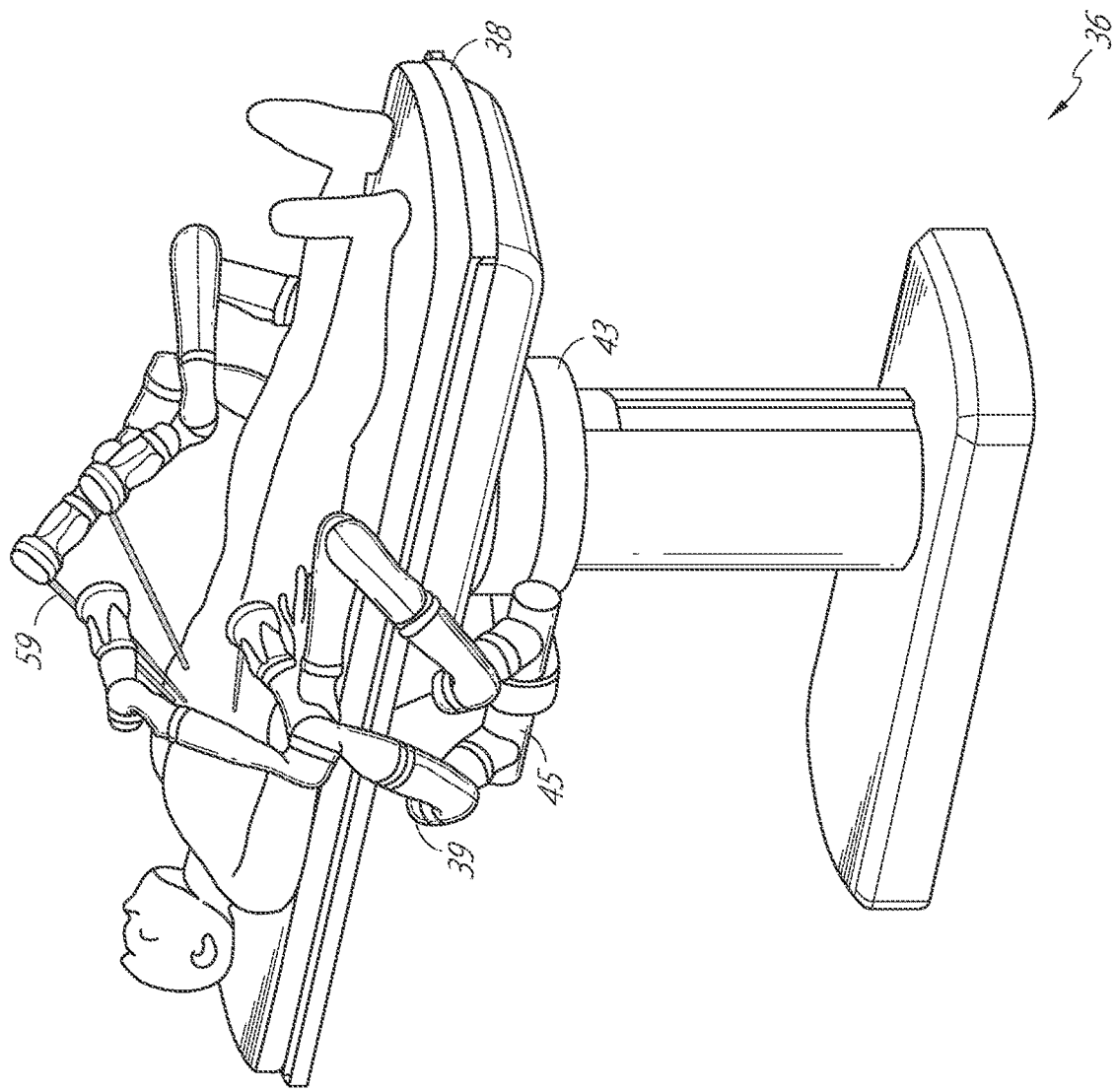
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
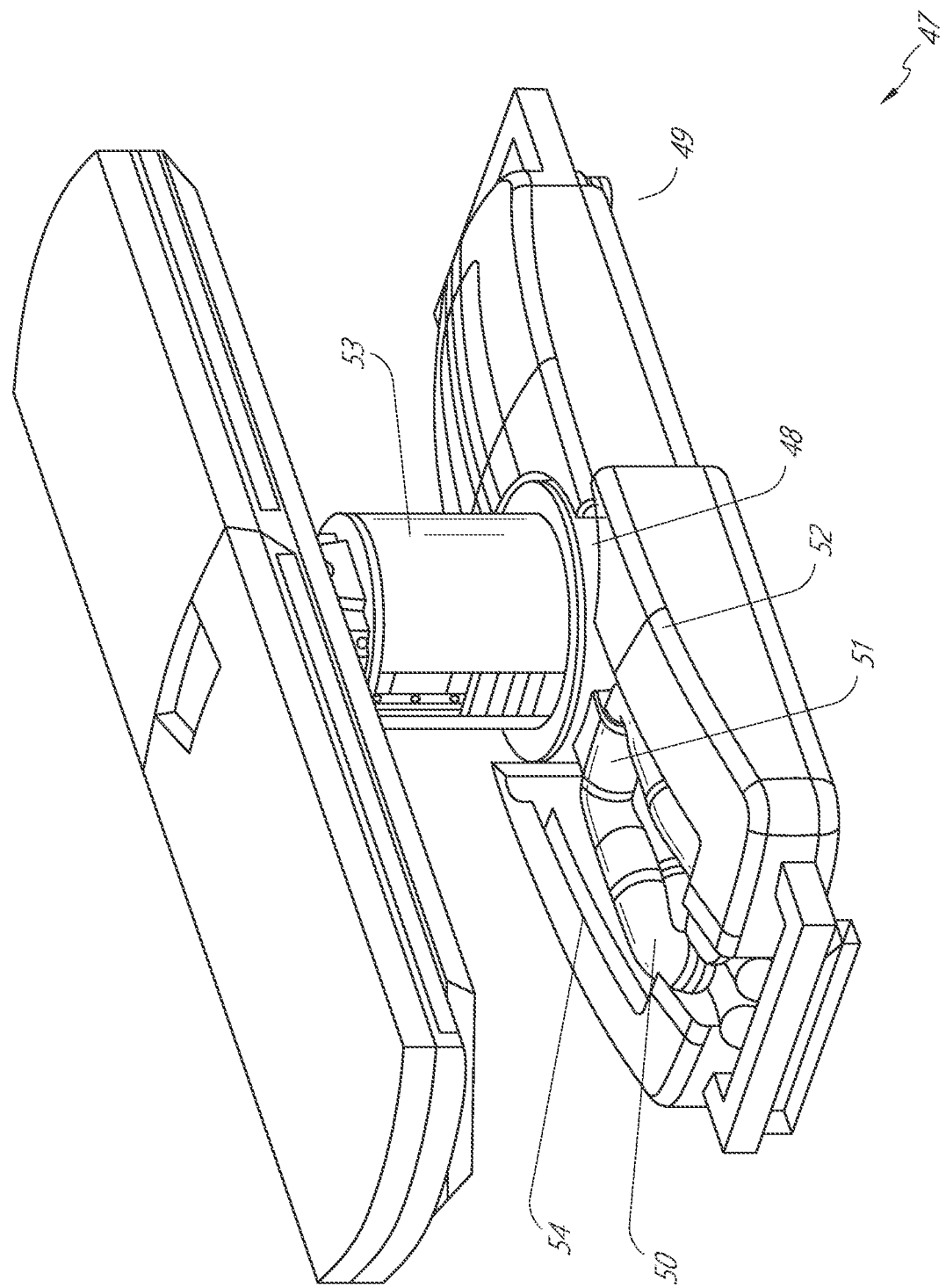
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
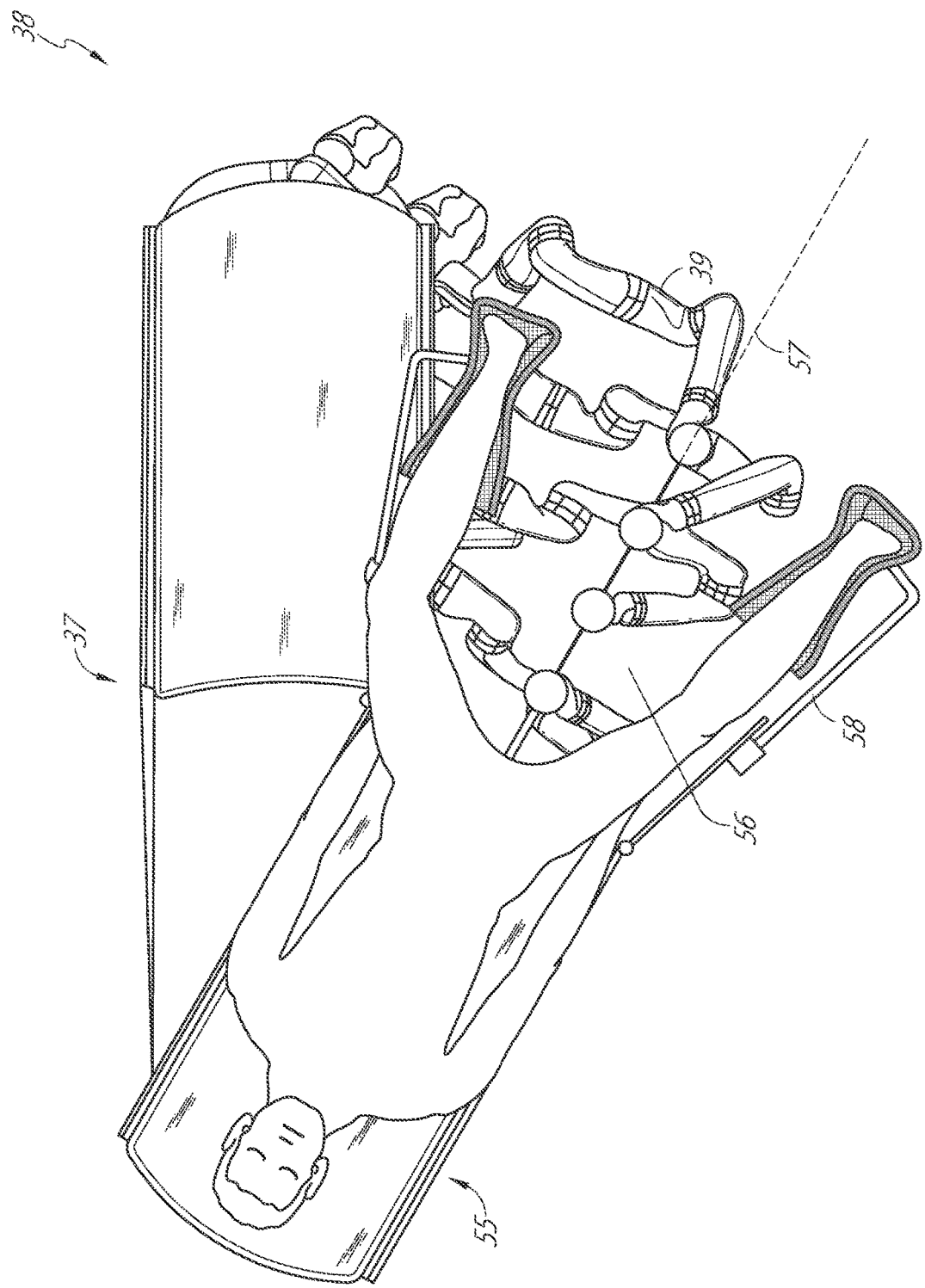
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
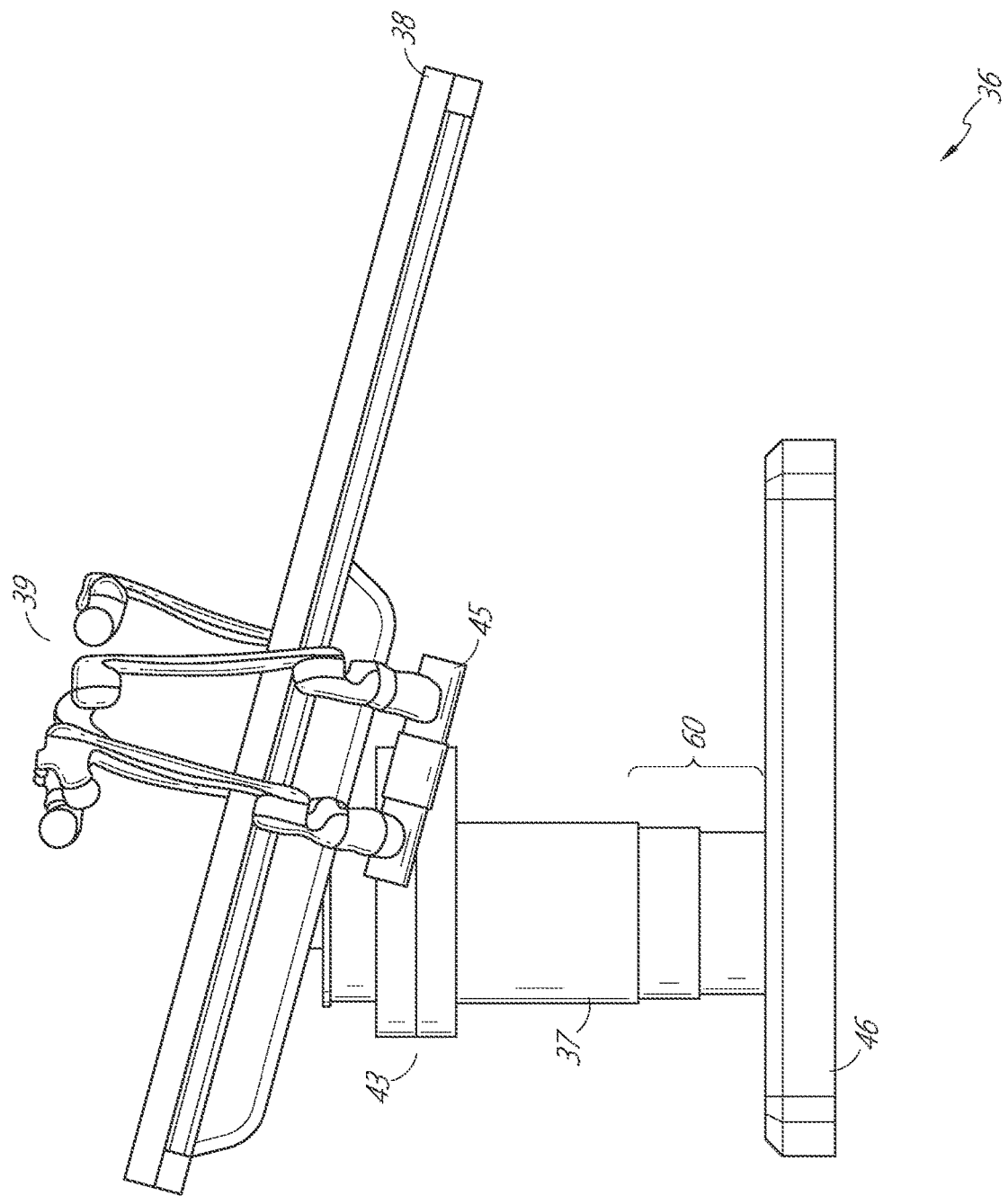
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
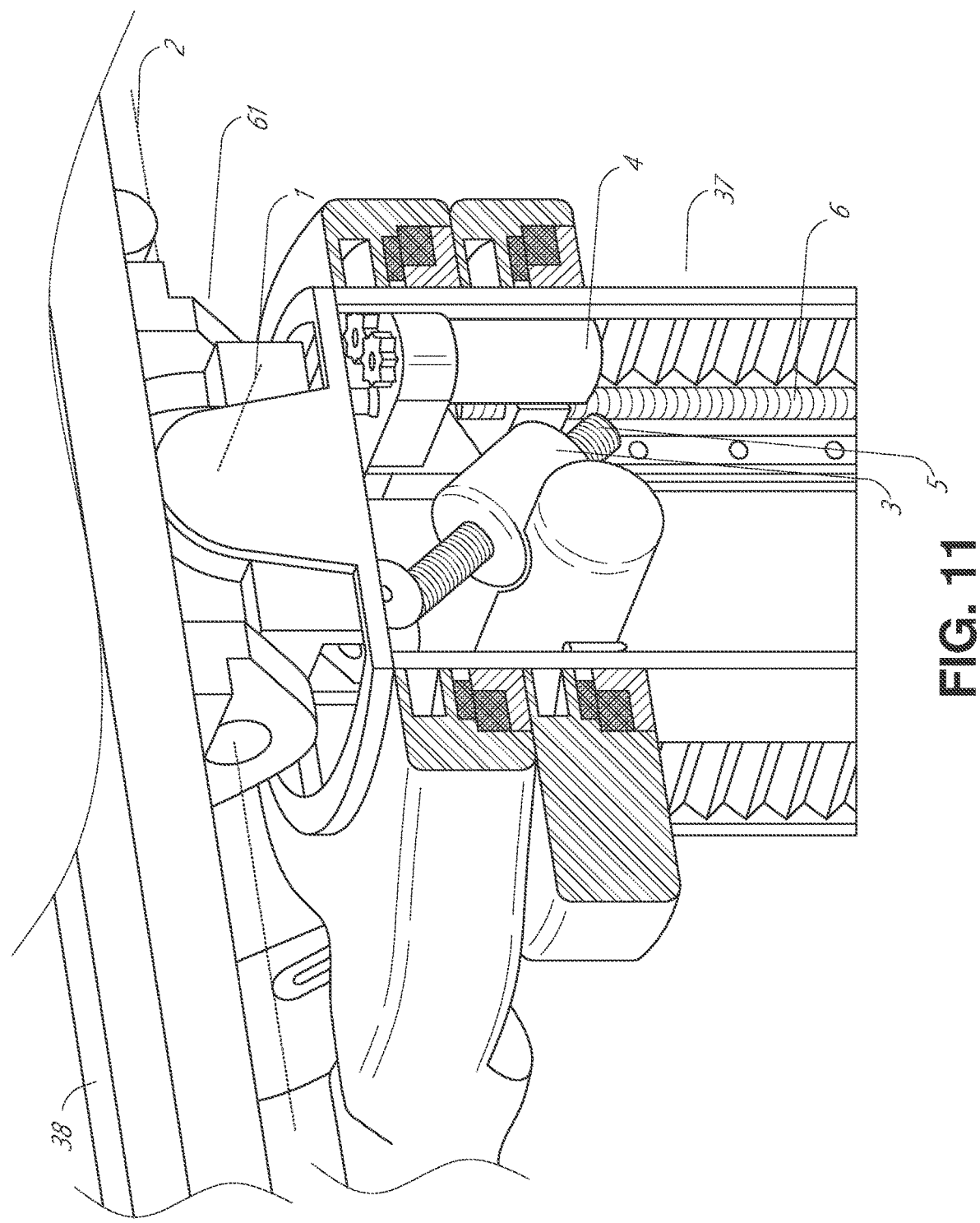
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
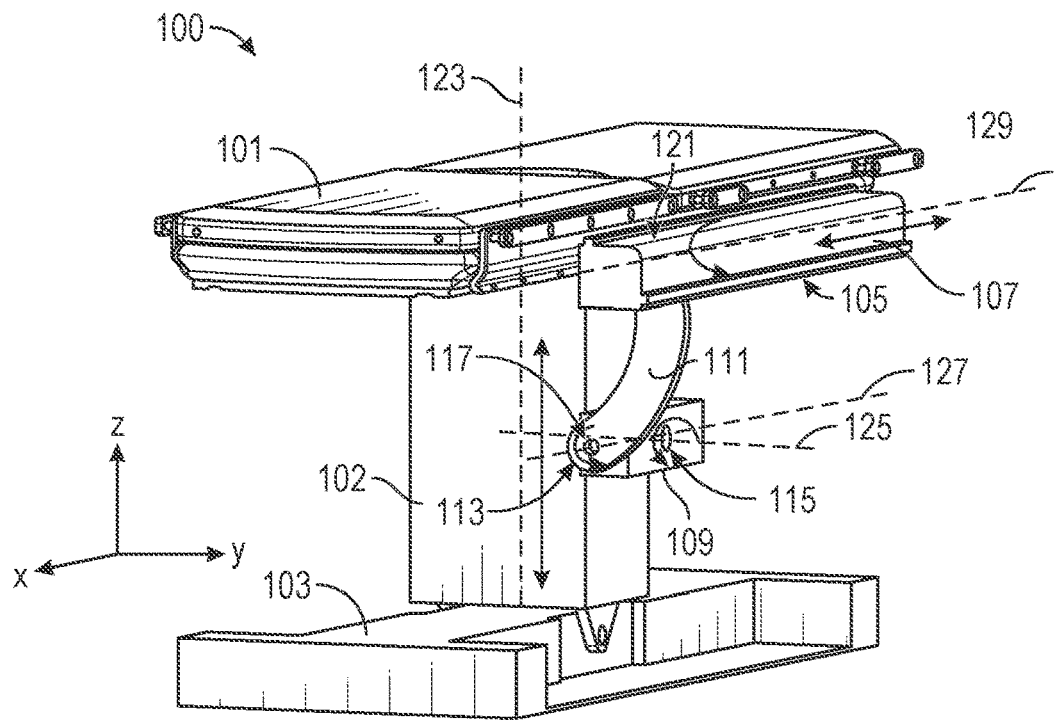
FIG. 12 illustrates an alternative embodiment of a table-based robotic system.
Figure 13:
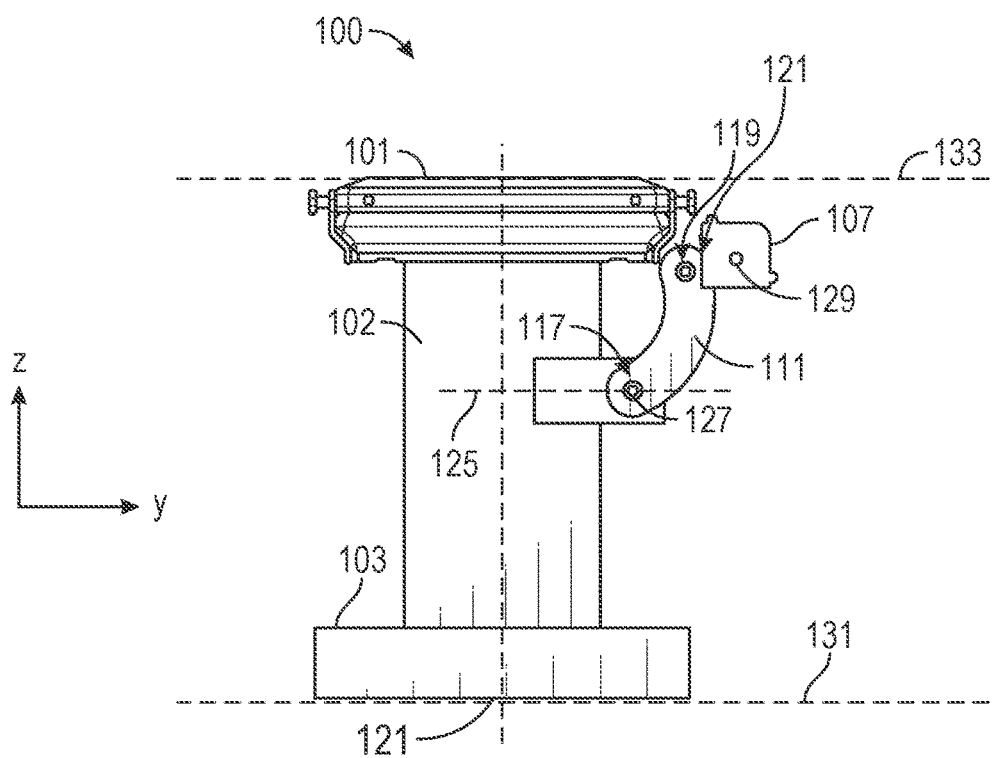
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
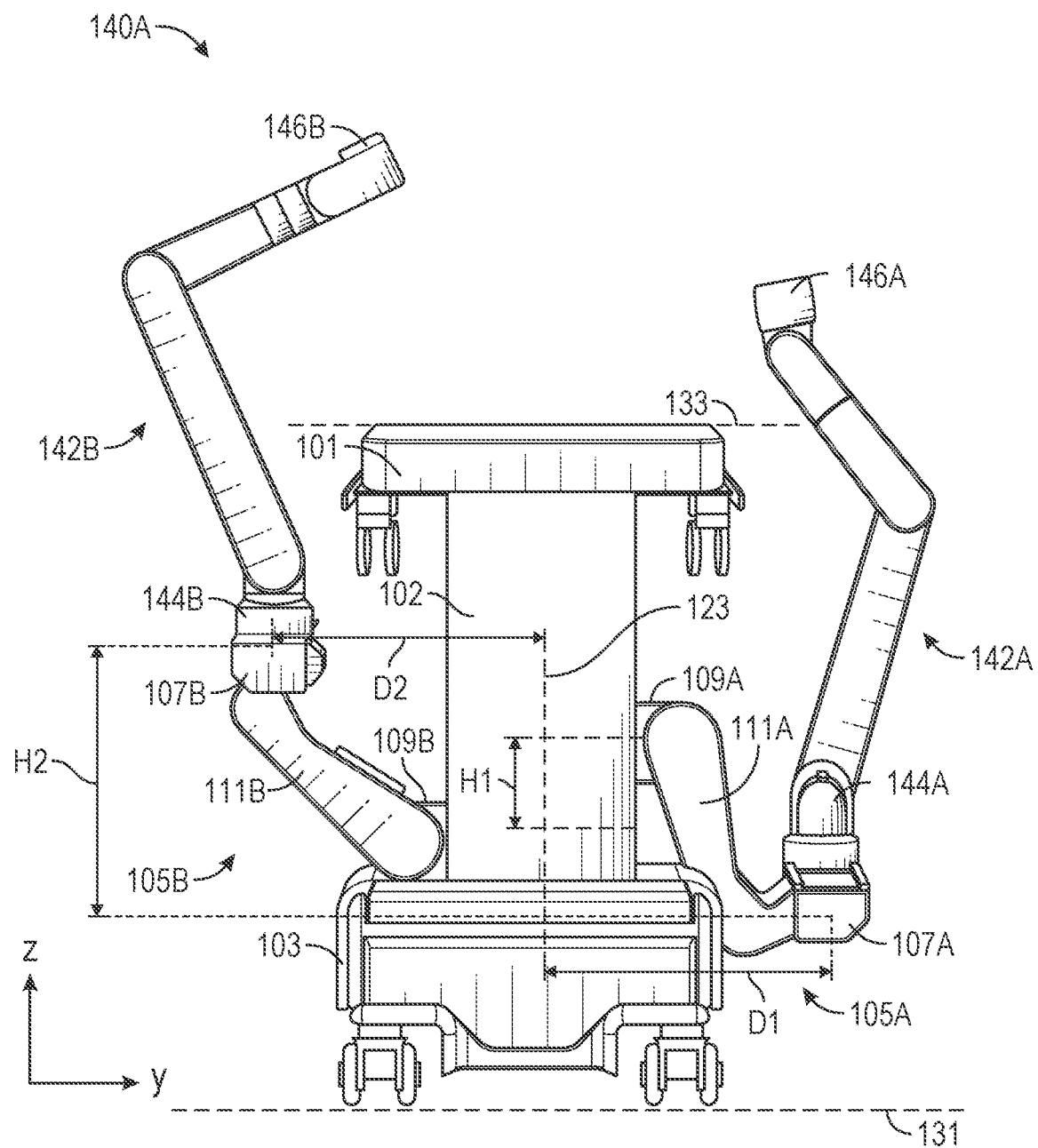
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
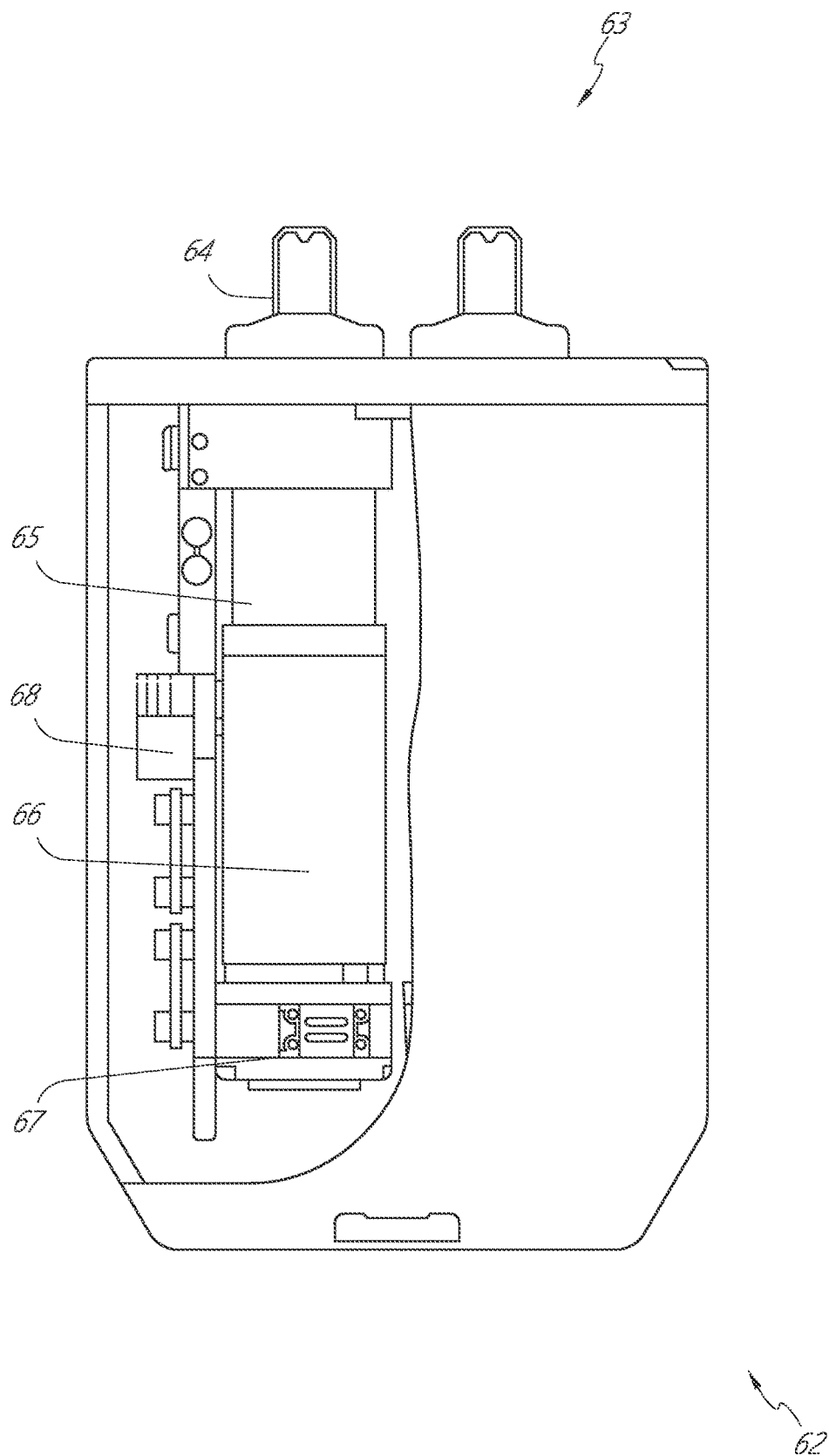
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
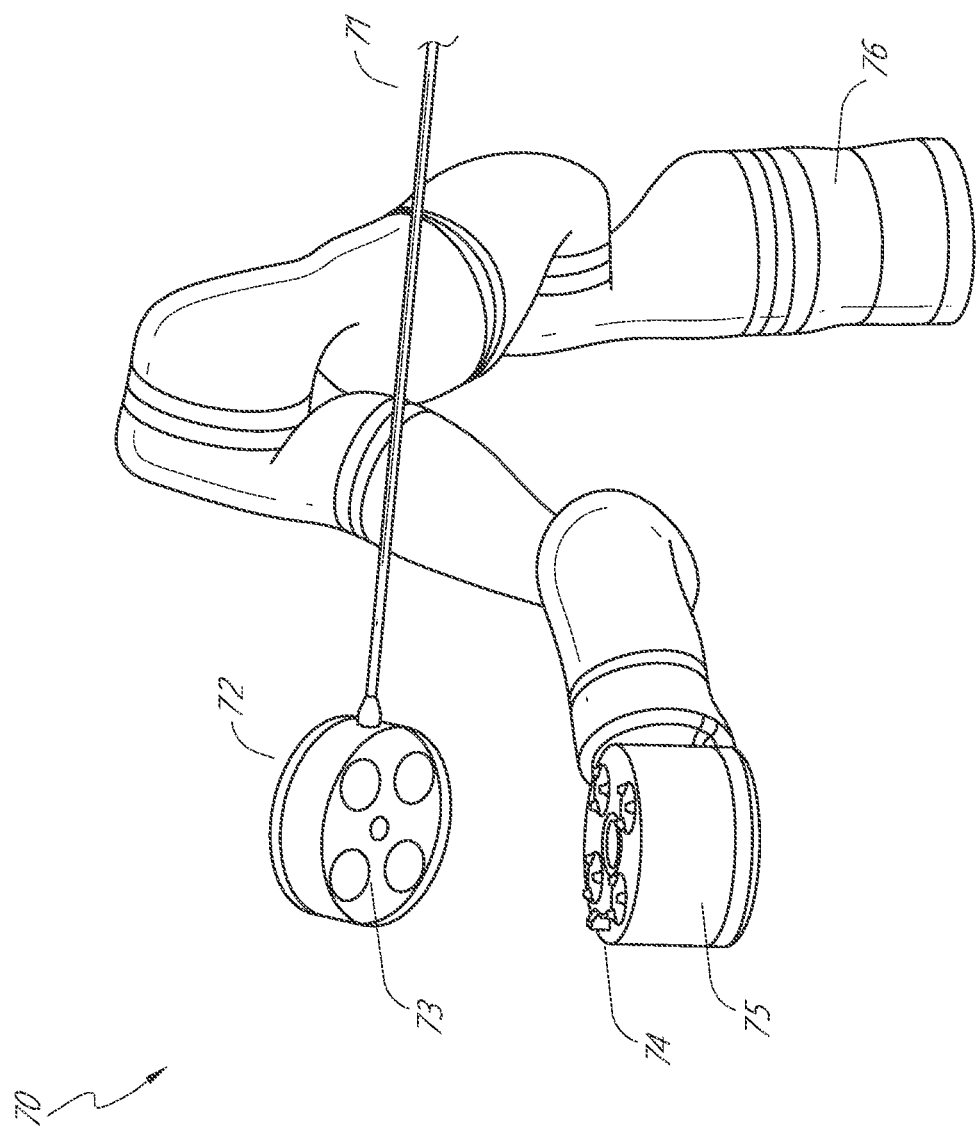
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
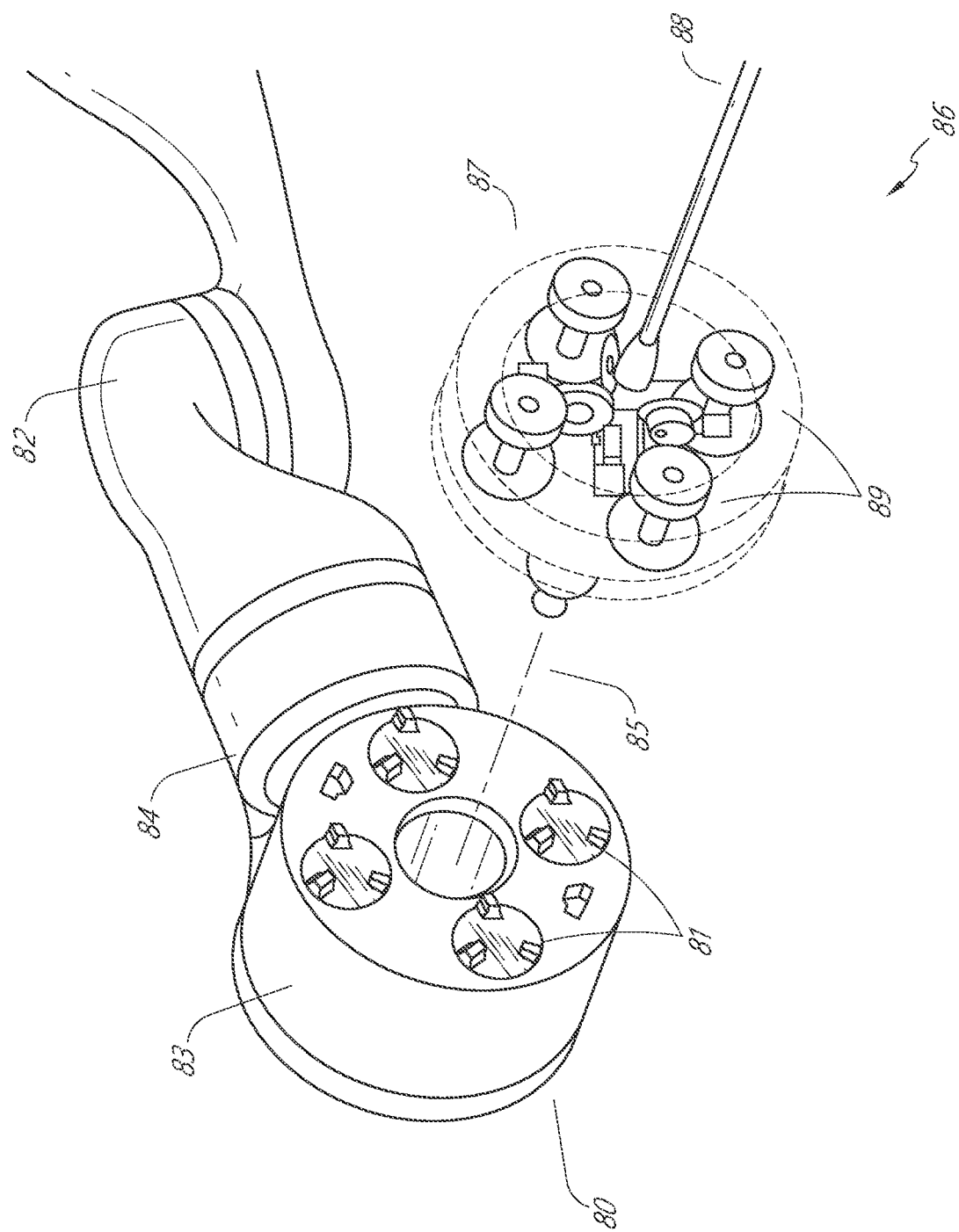
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
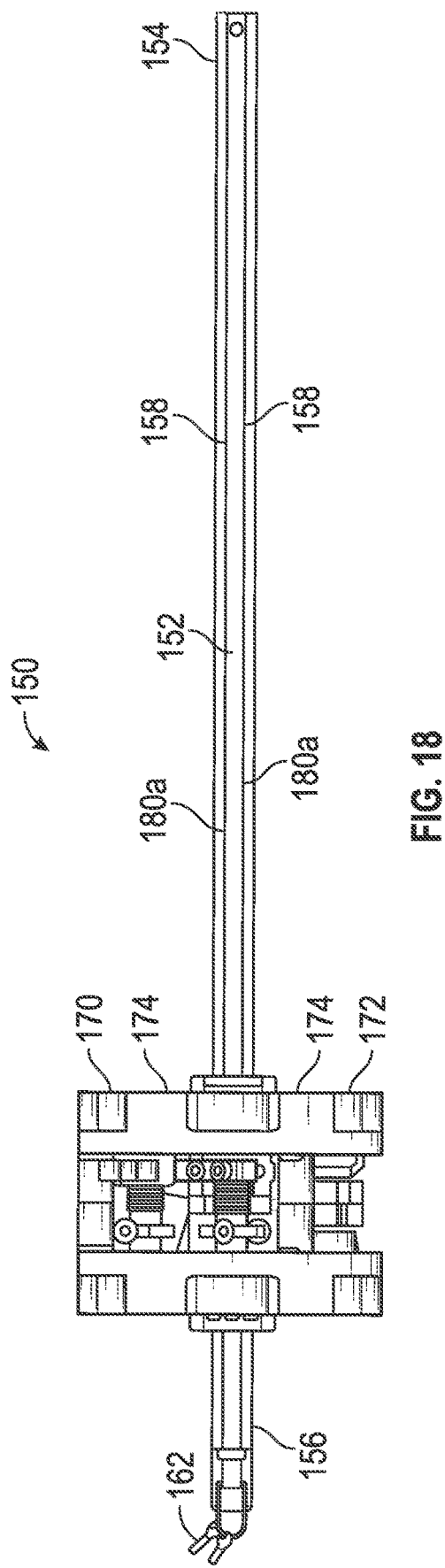
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
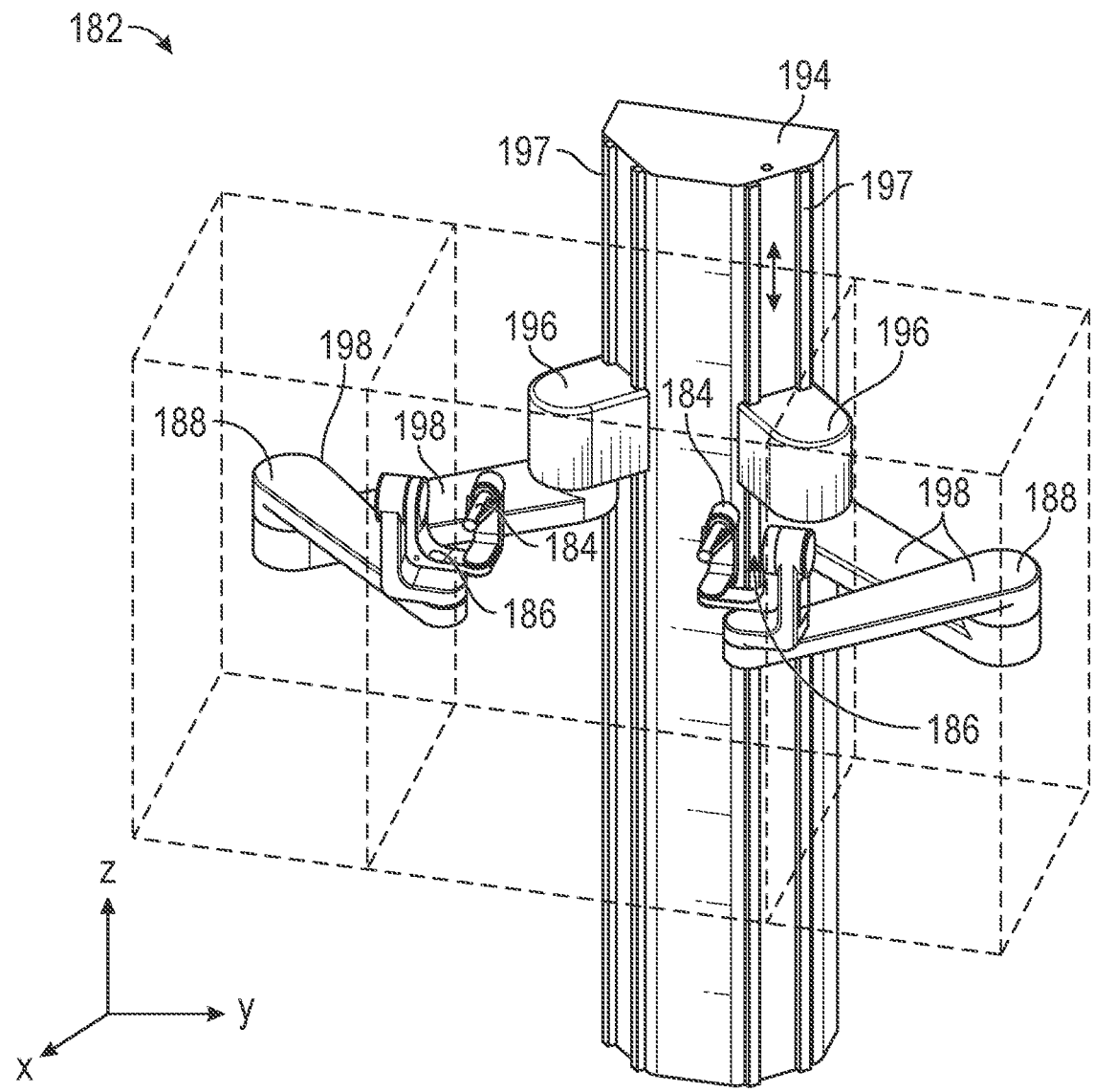
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
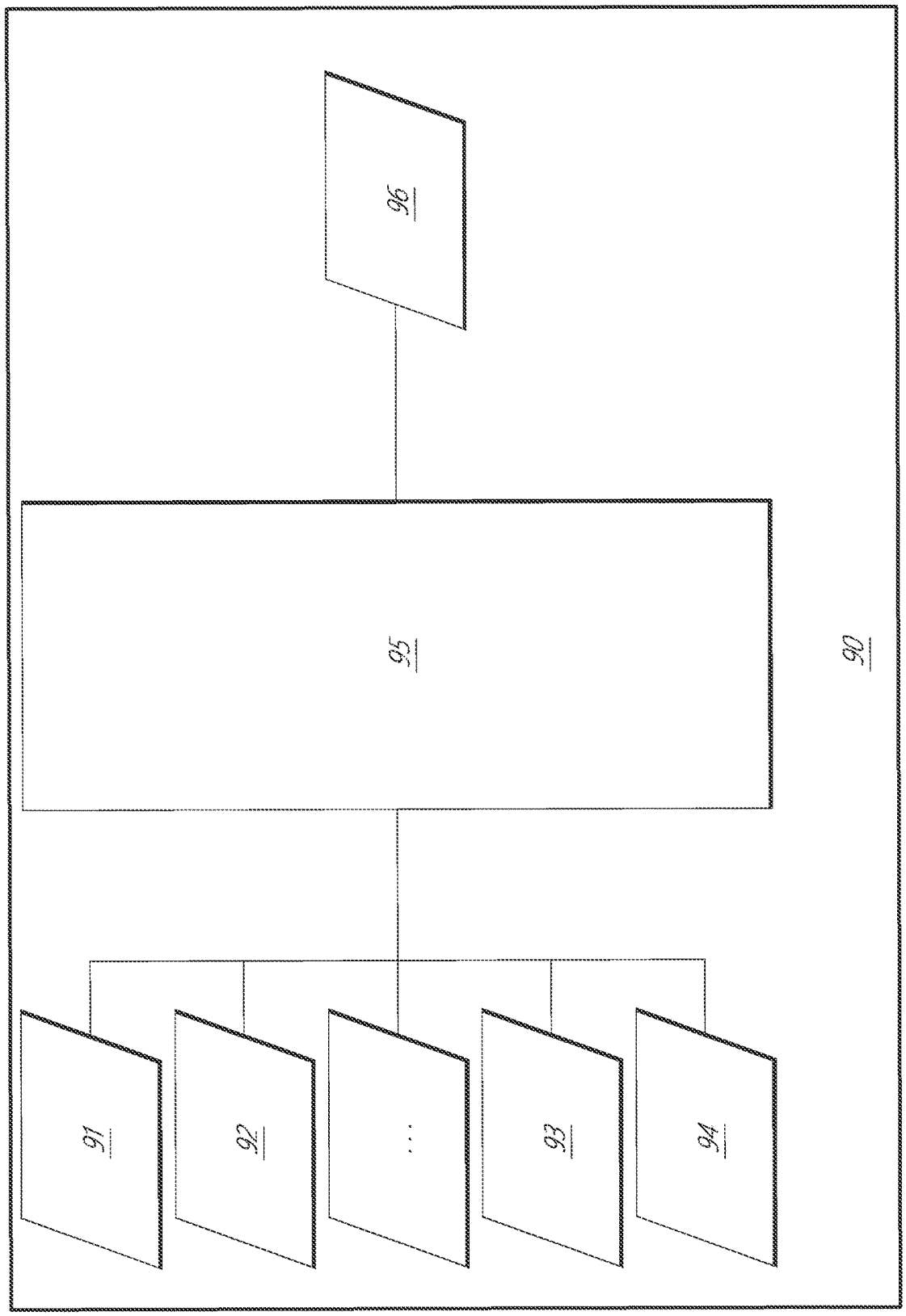
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Systems and Methods for Kinematic Optimization with Shared Robotic Degrees-of-Freedom (DoFs)

The present disclosure relates to systems and techniques for kinematic optimization with shared robotic DoFs. In some embodiments, the present disclosure relates to system and techniques for collision avoidance with shared robotic arm DOFs. Robotic arms may be used to achieve a desired pose (i.e., position and orientation) of an end effector of a medical tool. In some implementations, the medical tool may include a medical instrument or a camera. In manipulating a robotic arm to achieve the desired end effector pose, there may be a risk that some portion of the robotic arm is moved into a pose that would collide with another nearby object (e.g., another robotic arm, the patient, a platform supporting the patient, medical accessories attached to the platform, etc.).

One way to avoid robotic arm collisions is to position the robotic arms and access points, e.g., prior to performing a medical procedure, in such a way that the robotic arms are unlikely to be placed into a pose that would result in a collision. However, pre-procedure placement or positioning may limit the options for robotic arm placement and/or access point placement. For example, robotic arms and access points may be spaced apart by minimum distances in order to reduce the likelihood of collisions therebetween. However, such spacing of the robotic arms and/or access points may reduce the ability of the user to position medical tool(s) in desired pose(s). For example, certain procedures for patient of certain sizes (e.g., smaller patients) may involve close spacing of ports to form access points into the patient's anatomy. In these cases, it may not be possible to place the robotic arms and/or access points in locations that reduce the likelihood of robotic arm collisions.

Figure 21:
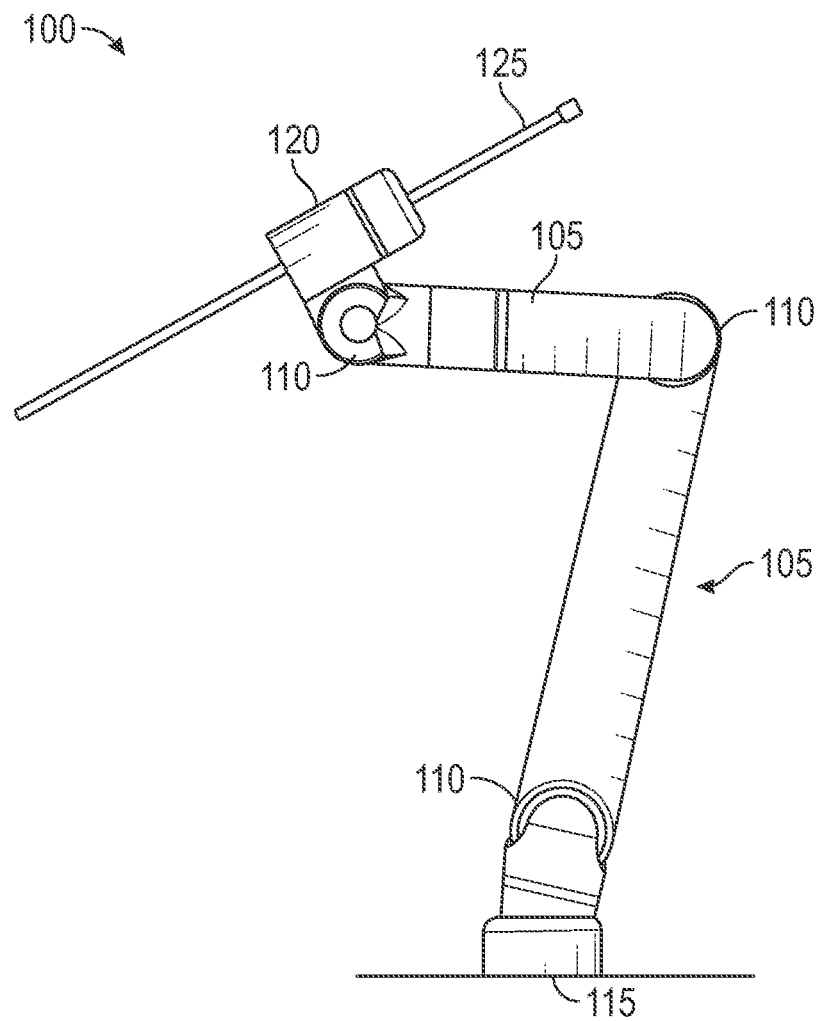
FIG. 21 illustrates an exemplary robotic arm in accordance with aspects of this disclosure.

FIG. 21 illustrates an exemplary robotic arm 100 in accordance with aspects of this disclosure. The robotic arm 100 includes a plurality of links 105 which are connected by one or more joints 110. A proximal end of the robotic arm 100 may be connected to a base 115 and a distal end of the robotic arm 100 may be connected to an advanced device manipulator (ADM) 120 (also referred to as an end effector). The ADM 120 may be configured to control the positioning and manipulation of a medical tool 125 (also referred to as a medical instrument). Thus, the links 105 may be detachably coupled to the medical tool 125. The joints 110 provide the robotic arm 100 with a plurality of DoFs that facilitate control of the medical tool 125 via the ADM 120.

During a medical procedure, it can be desirable to have the ADM 120 of the robotic arm 100 and/or a remote center of movement (RCM) of the tool 125 coupled thereto kept in a static pose/position. An RCM may refer to a point in space where a cannula or other access port through which a medical tool 125 is inserted is constrained in motion. In some implementations, the medical tool 125 includes an end effector that is inserted through an incision or natural orifice of a patient while maintaining the RCM.

In some circumstances, a robotic system can be configured to move one or more links 105 of the robotic arm 100 within a "null space" to avoid collisions with nearby objects (e.g., other robotic arms) while the ADM 120 of the robotic arm 100 and/or the RCM are maintained in their respective poses/positions. The null space can be viewed as the space in which a robotic arm 100 can move that does not result in movement of the ADM 120 and/or RCM, thereby maintaining the position and/or the orientation of the medical tool 125. In some implementations, a robotic arm 100 can have multiple positions and/or configurations available for each pose of the ADM 120.

For a robotic arm 100 to move the ADM 120 to a desired pose in space, in certain implementations, the robotic arm 100 may have at least six DoFs—three DoFs for translation (e.g., X, Y, Z position) and three DoFs for rotation (e.g., yaw, pitch, and roll). In some implementations, each joint 110 may provide the robotic arm 100 with a single DoF, and thus, the robotic arm 100 may have at least six joints to achieve freedom of motion to position the ADM 120 at any pose in space. To further maintain the ADM 120 of the robotic arm 100 and/or the remote center or motion in a desired pose, the robotic arm 100 may further have at least one additional "redundant joint." Thus, in certain implementations, the system may include a robotic arm 100 having at least seven joints 110, providing the robotic arm 100 with at least seven DoFs. However, depending on the implementation, the robotic arm 100 may have a greater or fewer number of DoFs.

A robotic arm 100 having at least one redundant DoF may refer to a robotic arm 100 can has at least one more DoF than the minimum number of DoFs for performing a given task. For example, a robotic arm 100 can have at least seven DoFs, where one of the joints 100 of the robotic arm 100 can be considered a redundant joint. The one or more redundant joints can allow a robotic arm 100 to move in a null space to both maintain the pose of the ADM 120 and a position of an RCM and avoid collision(s) with other arms or objects.

A robotic system (e.g., the system 36 of FIG. 6 or the system 140A of FIG. 14) can be configured to perform collision avoidance to avoid collision(s), e.g., between adjacent robotic arms by taking advantage of the movement of one or more redundant joints in a null space. For example, when a robotic arm collides with or approaches (e.g., within a defined distance of) another robotic arm, one or more processors of the system can be configured to detect the collision or impending collision (e.g., via kinematics). Accordingly, the system can control one or both of the robotic arms to adjust their respective joints within the null space to avoid the collision or impending collision. In one implementation involving a pair of robotic arms, a base of one of the robotic arms and its end effector can stay in its pose, while links or joints therebetween move in a null space to avoid collisions with an adjacent robotic arm.

In certain implementations, robotic systems may use the redundant joints in the robotic arms as the sole null space DoF. When the system has only one DoF of null space motion, the null space may be a one-dimensional line through space. If the null space line takes one or more of the robotic arm(s) through an invalid pose or into a collision, the system may not be able to provide null space adjustment and collision avoidance for certain ADM poses and/or RCM positions.

Aspects of this disclosure relate to the use of DoFs from different types of robotic components for kinematic optimization, such as collision avoidance. In particular, certain aspects of this disclosure relate to collision avoidance using DoFs of a robotic medical system which are shared between different robotic components. As used herein, shared DoFs may refer to DoFs which affect the pose of at least two separate end effectors. For example, the robotic system may include an adjustable arm support on which one or more robotic arms are supported. The adjustable arm support may have DoFs which are shared with the robotic arms supported by the adjustable arm support. In another example, the robotic system may include an adjustable patient platform that is moveable in one or more DoFs which are shared with one or more robotic arms coupled to a support structure that supports the patient platform.

Figure 22:
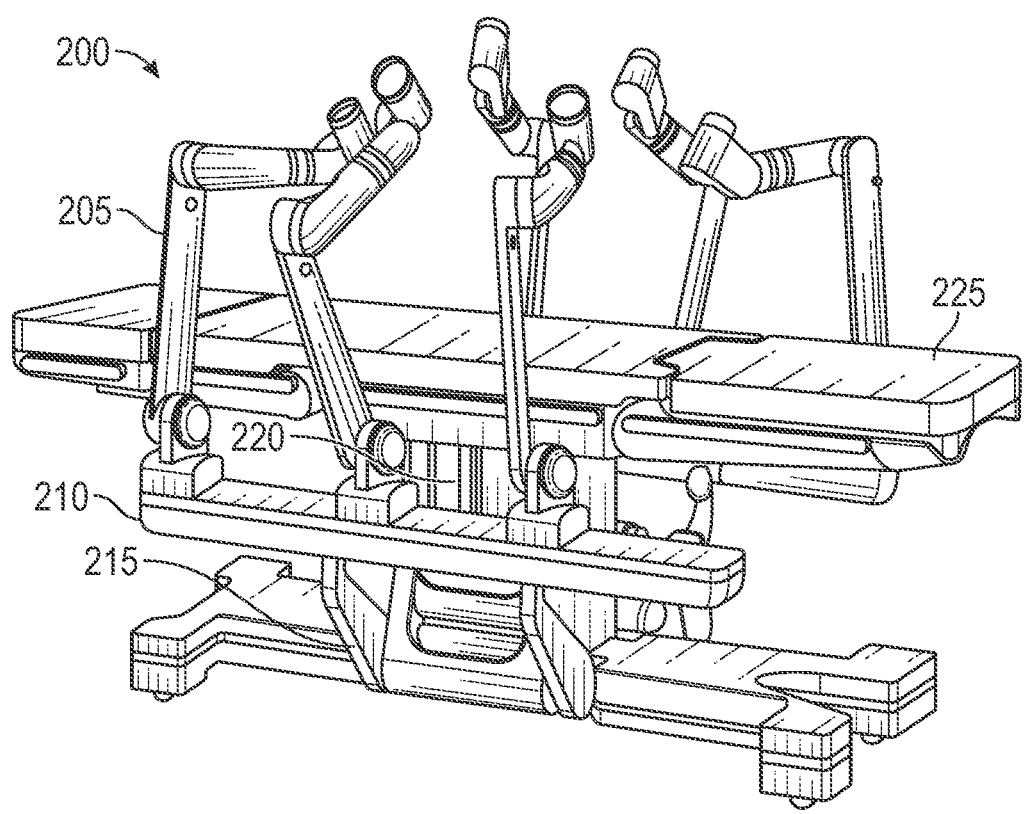
FIG. 22 illustrates an example of a robotic system including an adjustable arm support in accordance with aspects of this disclosure.

FIG. 22 illustrates an example of a robotic system 200 including an adjustable arm support 210 in accordance with aspects of this disclosure. With reference to FIG. 22, the robotic system 200 includes a plurality of robotic arms 205, one or more adjustable arm supports 210, one or more set-up joints 215, and a bed column 220. Each of the robotic arms 205 may be supported by one of the adjustable arm supports 210 and the adjustable arm support(s) 210 may be in turn supported by the set-up joint(s) 215. As described above, each robotic arm 205 may have a plurality of DoFs. Similarly, the adjustable arm support(s) 210 and the set-up joint(s) 215 may be moveable in one or more DoFs.

Figure 23:
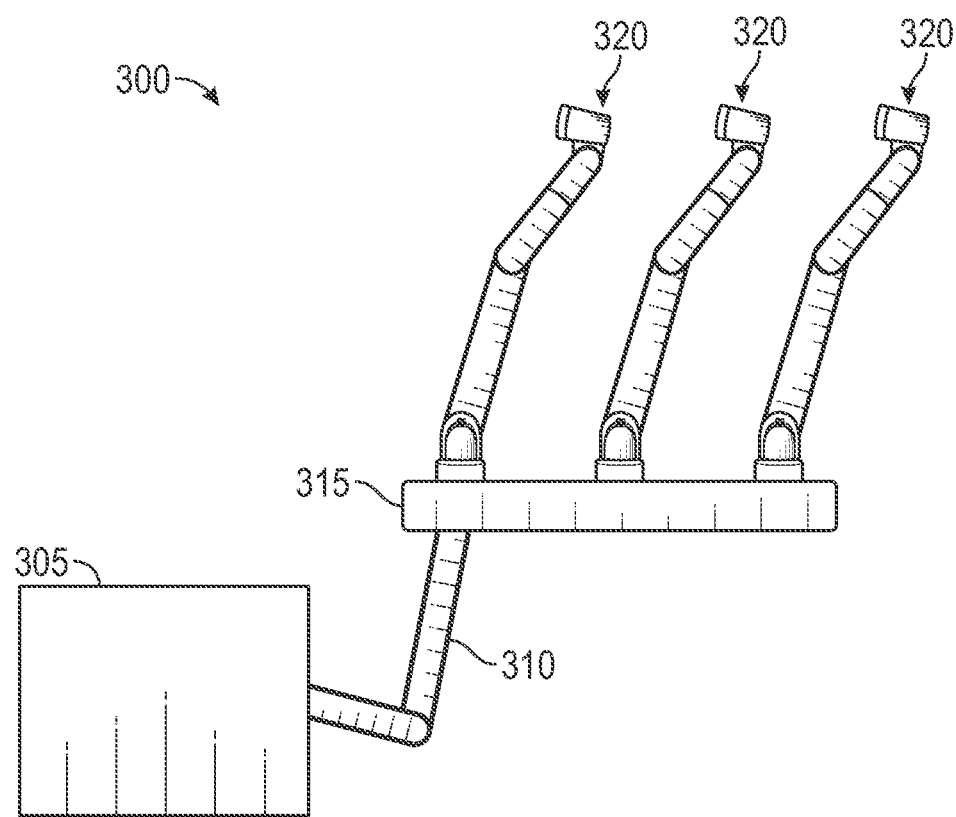
FIG. 23 schematically illustrates how one or more degrees-of-freedom (DoFs) can be shared between robotic arms, an adjustable arm support, and a set-up joint.

FIG. 23 schematically illustrates how one or more DoFs can be shared between robotic arms, an adjustable arm support, and a set-up joint. FIG. 23 shows a system 300 where a set-up joint 310 may be coupled to a bed support 305 at a proximal end and to an adjustable arm support 310 at a distal end. Further, a plurality of robotic arms 320 may be coupled to the adjustable arm support 315 at their respective proximal ends. In certain implementations, the adjustable arm support 315 and the set-up joint 310 together may have four DoFs. Thus, the robotic arms 320 attached to the adjustable arm support 315 may share the four DoFs provided by the set-up joint 310 and the adjustable arm support 315.

Another example of a robotic system 100 including an adjustable arm support 105 in accordance with aspects of this disclosure is illustrated in FIG. 12. The adjustable arm support 105 can provide several degrees of freedom, including lift, lateral translation, tilt, etc. In the illustrated implementation of FIG. 12, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The carriage 109 can be attached to the column 102 by a first joint 113, which allows the carriage 109 to move relative to the column 102 (e.g., such as up and down a first or vertical axis). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint (not illustrated) can be provided that mechanically constrains the third joint 117 to maintain an orientation of the rail 107 as the rail connector 111 is rotated about a third axis. The adjustable arm support 105 can include a fourth joint 121, which can provide a fourth degree of freedom (translation) for the adjustable arm support 105 along a fourth axis.

Thus, dependent on the implementation, a robotic medical system can have many more robotically controlled degrees of freedom beyond just those in the robotic arms to provide for null space movement and collision avoidance. In each of these implementations, the end effectors of one or more robotic arms (and any tools or instruments coupled thereto) and/or a remote center of a tool associated therewith can advantageously maintain in pose and/or position within a patient.

A. Null Space Movement Between Link Members Using Shared Robotic DoFs.

Aspects of this disclosure relate to robotic systems and methods utilize shared DoFs between different link members (e.g., of a plurality of robotic arms and/or an adjustable arm support) to achieve null space movement for collision avoidance. In certain implementations, the system can use one or more DoFs associated with a first set of one or more motorized links (e.g., in the form of one or more robotic arms—e.g., the robotic arms 205 illustrated in FIG. 22) in coordinated and/or synchronized motion with one or more DoFs associated with a second set of one or more motorized links (e.g., in the form of support links that support the robotic arms, including one or more set-up joint links and one or more arm support links—e.g., the set-up joint 215 and adjustable arm support 210 illustrated in FIG. 22) to achieve null space movement for collision avoidance.

The first set of one or more motorized links (e.g., in the form of one or more robotic arms) can be configured to perform a different function from the second set of one or more motorized links (e.g., in the form of support links or rails). In some implementations, the first set of one or more links is supported by the second set of one or more links.

Moreover, in some implementations, the first set of one or more motorized links has a different number of DoFs from the second set of one or more motorized links. For example, in the as shown in the simplified implementation illustrated in FIG. 23, the first set of one or more links may form three robotic arms 320 each having 7 or more DoFs. For example, each of the robotic arms 320 may have DoFs including but not limited to shoulder yaw, shoulder pitch, elbow pitch, wrist yaw, wrist pitch, roll, and insertion. The second set of one or more motorized links may form a set-up joint 310 in combination with an adjustable arm support 315 having 4 or more DoFs. For example, the set-up joint 310 and the adjustable arm support 315 may have DoFs including but not limited to vertical translation or "Z-lift," longitudinal translation along the bed, tilt, and upward pivot. The DoFs of the set-up joint 310 and adjustable arm support 315 are also illustrated in FIG. 24, as discussed above.

In other implementations, the first set of one or more motorized links can have the same number of DoFs as the second set of one or more motorized links. Advantageously, by sharing DoFs between the first set of one or more links with DoFs and the second set of one or more links, the number of DoFs for null space movement and collision avoidance can be expanded.

Aspects of this disclosure relate to robotic systems have one or more DoFs in addition to the DoFs of the robotic arms that are capable of null space movement. These extra DoFs (e.g., from the set-up joint in combination with the adjustable arm support) can affect the motion of the robotic arm(s) coupled to the adjustable arm support and assist in collision avoidance. For example, the DoFs from the second set of links including vertical translation, longitudinal translation, and tilt can be particularly useful for null space movement when combined with the DoFs of each of the robotic arms.

In the implementations described above, the shared DoFs between different sets of link members are utilized for null space movement whereby at least one set of link members is associated with a robotic arm. In these implementations, the ADM of the robotic arm, as well as an RCM of a tool attached thereto, can advantageously be kept in pose/position.

Figure 24B:
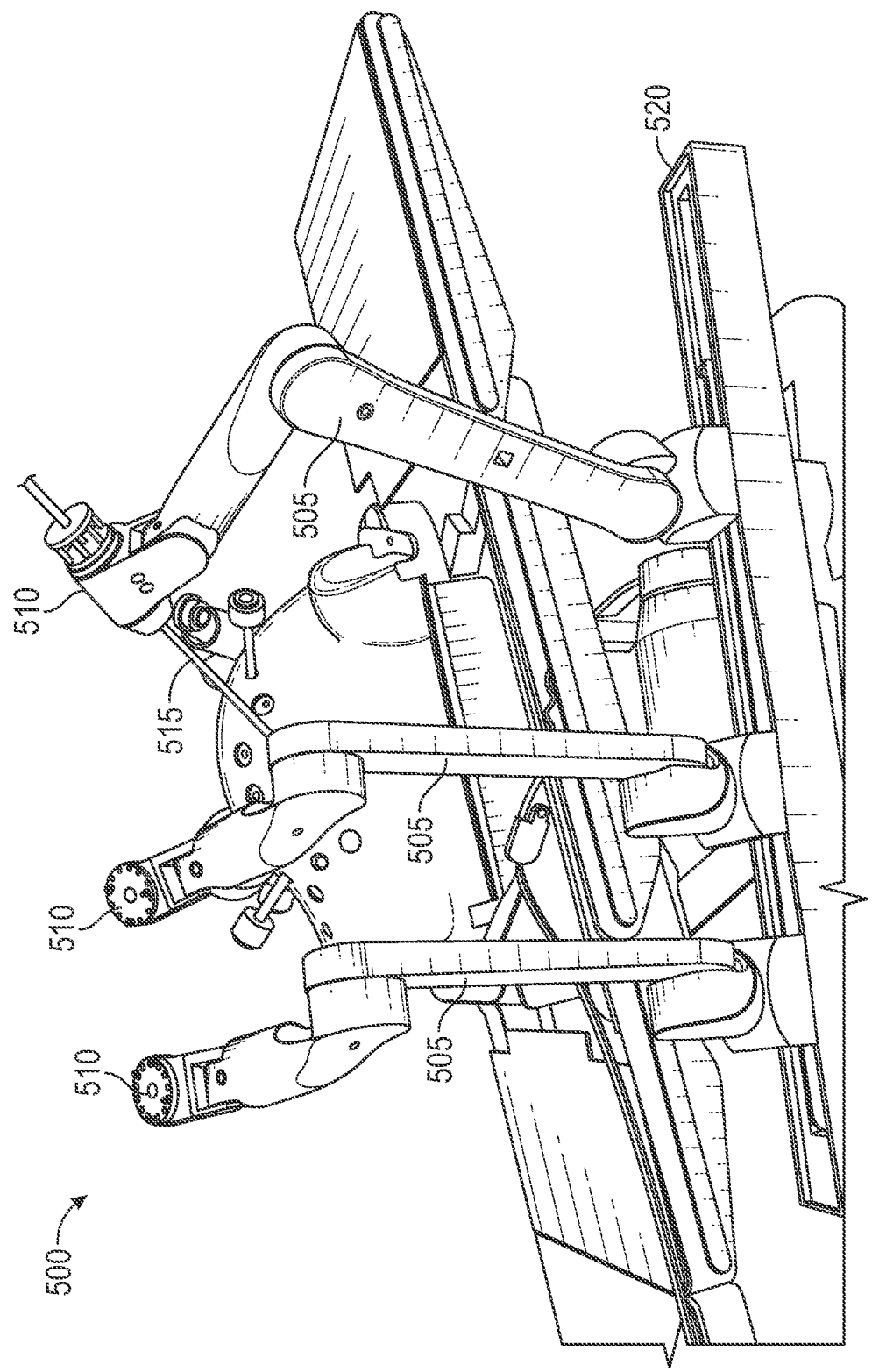

FIGS. 24A and 24B illustrate the movement of two sets of links while maintaining ADM and RCM poses/positions in accordance with aspects of this disclosure. Specifically, FIG. 25A illustrates a robotic system 500 including a plurality of robotic arms 505 formed by a first set of links, each having an ADM 510 configured to control movement of a medical tool 515. The robotic arms 505 are supported by an adjustable arm support 520 and a set-up joint (not illustrated) formed by a second set of links. FIG. 24A illustrates the poses of each of the robotic arms 505, the ADMs 510, the medical tool 515, and the adjustable arm support at a first point in time.

FIG. 24B illustrates the robotic system 500 of FIG. 24A at a second point in time after the first and second sets of links have been moved in null space. As can be seen in a comparison of FIGS. 24A and 24B, the pose (including the position and rotation) of each of the ADMs and the medical tool 515 is maintained while the robotic arms 505 and the adjustable arm support 520 are moved in null-space. The shared DoFs between the first and second sets of links allow for null space movement of one or more of the robotic arms 505, the adjustable arm support 520, and the set-up joint while maintaining the poses/positions of the ADMs and an RCM of the medical tool 515. Thus, the system is able to maintain the poses of the ADM 510 of the robotic arms 505 and the medical tool 515, even when there is movement (e.g., via the shared DoFs) between the first set of link members (e.g., the robotic arms 505) and the second set of link members (e.g., the set-up joint and the adjustable arm support 520).

Figure 25:
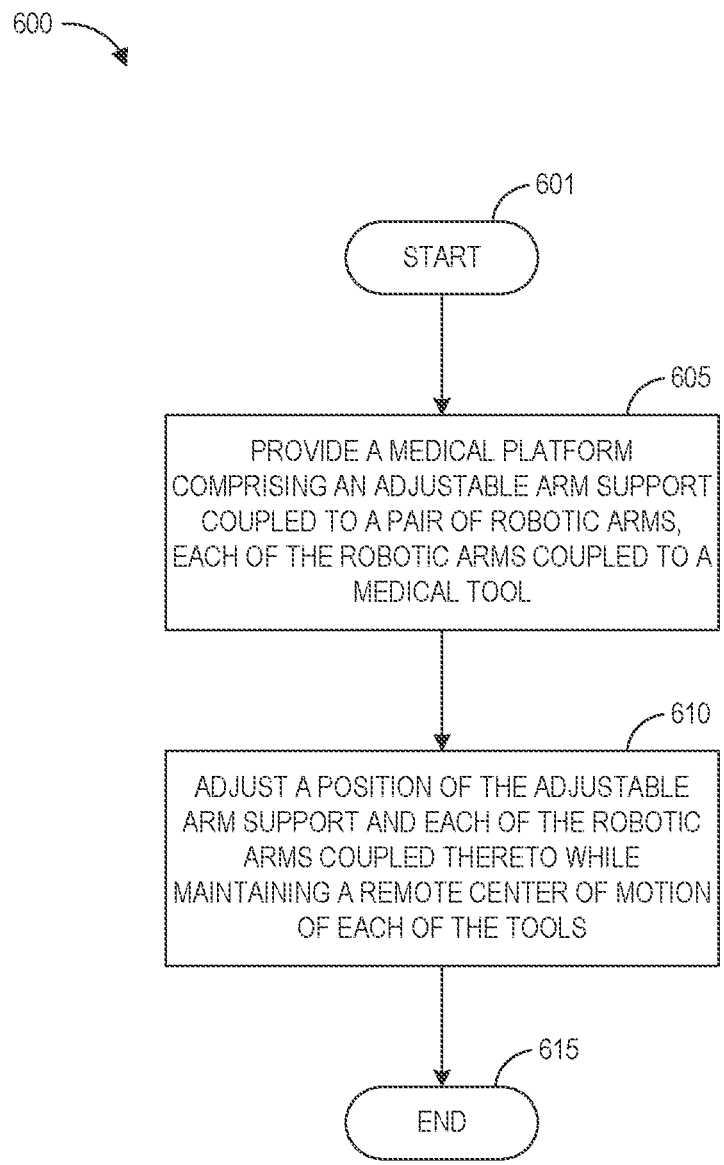
FIG. 25 is a flowchart illustrating an example method operable by a robotic system, or component(s) thereof, for null space movements between link members using shared robotic DoFs in accordance with aspects of this disclosure.

FIG. 25 is a flowchart illustrating an example method operable by a robotic system, or component(s) thereof, for null space movements between link members using shared robotic DoFs in accordance with aspects of this disclosure. For example, certain steps of method 600 illustrated in FIG. 25 may be performed by processor(s) and/or other component(s) of a medical robotic system (e.g., robotically-enabled system 10) or associated system(s). For convenience, the method 600 is described as performed by the "system" in connection with the description of the method 600.

The method 600 begins at block 601. At block 605, the method 600 may involve providing a medical platform comprising an adjustable arm support coupled to a pair of robotic arms. Each of the robotic arms can be coupled to a medical tool. For example, the medical platform may be part of the system 200 illustrated in FIG. 22, the system 100 illustrated in FIG. 12, the system 500 illustrated in FIGS. 24A and 24B, or the system 200 illustrated in FIG. 22.

At block 610, the system may adjust a position of the adjustable arm support and each of the robotic arms coupled thereto while maintaining an RCM of each of the tools. For example, as shown in FIGS. 24A and 24B, the system may move the adjustable arm support 520 and the robotic arms 505 coupled thereto while maintaining the RCM of the medical tool 515. The method 600 ends at block 615.

Figure 26:
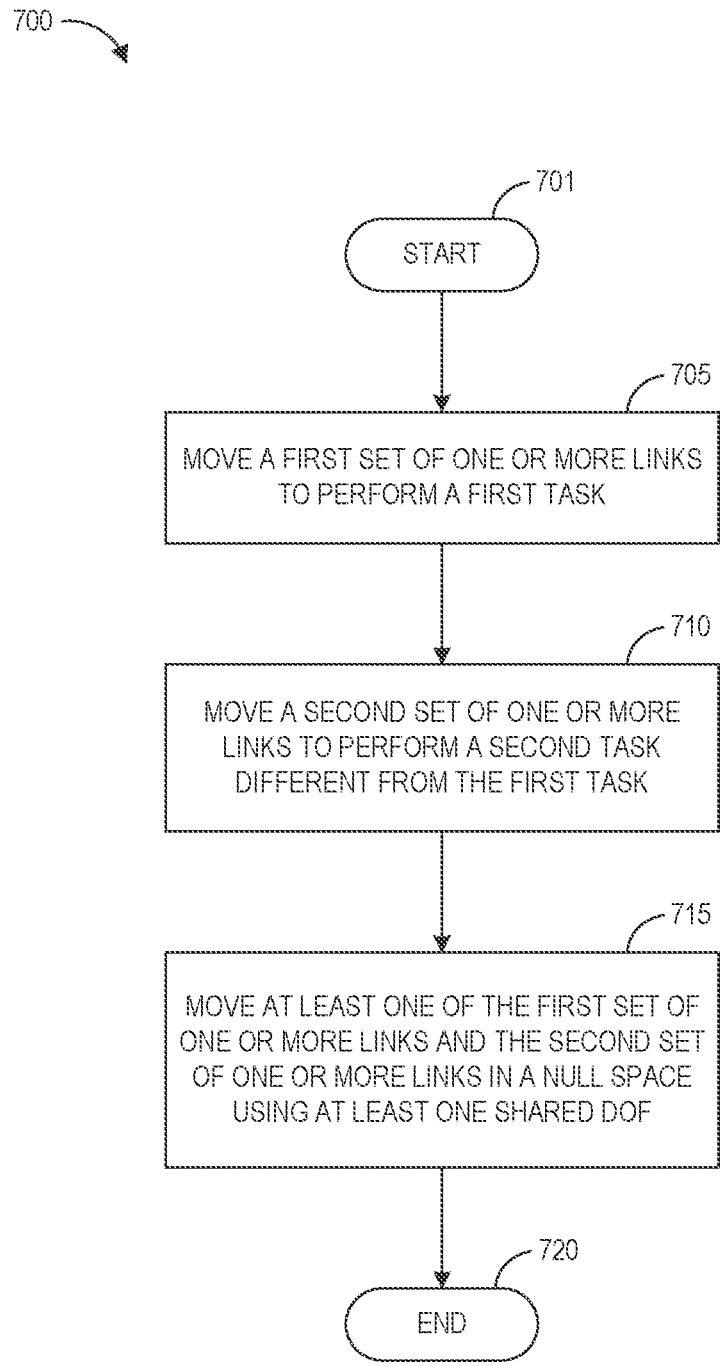
FIG. 26 is a flowchart illustrating another example method operable by a robotic system, or component(s) thereof, for null space movements between link members using shared robotic DoFs in accordance with aspects of this disclosure.

FIG. 26 is a flowchart illustrating another example method operable by a robotic system, or component(s) thereof, for null space movements between link members using shared robotic DoFs in accordance with aspects of this disclosure. For example, certain steps of method 700 illustrated in FIG. 26 may be performed by processor(s) and/or other component(s) of a medical robotic system (e.g., robotically-enabled system 10) or associated system(s). For convenience, the method 700 is described as performed by the "system" in connection with the description of the method 700.

The method 700 begins at block 701. At block 705, the system may move a first set of one or more links to perform a first task. The first set of one or more links can have at least one DoF. At block 710, the system may move a second set of one or more links to perform a second task different from the first task. The second set of one or more links can also have at least one DoF. The at least one DoF of each of the first set of one or more links and the second set of one or more links are shared.

At block 715, the system can move at least one of the first set of one or more links and the second set of one or more links in a null space using the shared at least one DoF. In some implementations, moving the first set of links in the null space may involve changing a configuration (e.g., a pose) of the first set of one or more links while maintaining a position of an end effector of one or more robotic arms. The method 700 ends at block 720.

In some implementations of the method 700, the first set of one or more links may include one or more robotic arms (e.g., at least three robotic arms) and the second set of one or more links may form support links. The system may move the robotic arms and/or the support links in order to avoid a collision between the arms and another object (e.g., another robotic arm or other object in the environment). Such collision avoidance may involve the system determining that movement of one or more of the robotic arms would position at least one of the robotic arms within a threshold distance of an object in the workspace. The system may further command movement of at least one of: (i) the at least three robotic arms and (ii) the second set of one or more links in the null space to reduce the likelihood of a collision involving the at least one robotic arm and the object within the workspace.

In certain implementations, the method 700 may further involve maintaining a position an RCM of a medical tool coupled to the first set of one or more links while moving the first set of one or more links in a first set of one or more DoFs. For example, it may be desirable to maintain an RCM such that the medical tool does not apply unnecessary force to a body wall of a patient. In some implementations, maintaining the RCM may involve maintaining the RCM the medical tool relative to an operating table. The method 700 may further involve maintaining the position of the RCM while moving the second set of one or more links in at least one second DoF, thereby allowing null space movement of the second set of one or more links.

In certain implementations, null space movement between at least one robotic arm and an adjustable arm support using shared DoFs may also be performed by a robotic medical system comprising a base, the adjustable arm support coupled to the base, and the at least one robotic arm coupled to the adjustable arm support. The at least one robotic arm can be configured to be coupled to a medical tool that is configured to be delivered through an incision or natural orifice of a patient (e.g., as shown in FIGS. 24A and 24B). The system may further include a processor configured to adjust a position of the adjustable arm support and the at least one robotic arm while maintaining an RCM of the tool. When the system includes two or more robotic arms, the processor may be configured to adjust a position of the adjustable arm support and each of the robotic arms while maintaining an RCM of each of the tools. By adjusting the positions of both the adjustable arm support and the robotic arm(s) simultaneously, the system may take advantage of the null space provided by at least one shared DoF between the robotic arm and the adjustable arm support to maintain the RCM of the tool.

The processor may further be configured to adjust the position of the adjustable arm support and the at least one robotic arm while maintaining a position of the end effector of the tool coupled to the at least one robotic arm. In some embodiments, the processor may be further configured to adjust the positions of the robotic arm and/or adjustable arm support which a position of a distal end of the tool is controlled by a clinician. For example, the processor may adjust the position of the adjustable arm support while the tool is teleoperatively controlled by the clinician.

The system may further be configured to move one or more of the robotic arm and the adjustable arm support for collision avoidance. For example, certain commanded tool positions may bring one of the robotic arms to collide with another robotic arm or another object in the environment. Since the additional or redundant DoFs provided by the robotic arms, adjustable arm support, and/or set-up joint allow for movement within null space (e.g., without changing the positions of the end effector of a tool and a remote center or movement), the system may move one or more of the robotic arms, adjustable arm support, and set-up joint to avoid the potential collision. Thus, in some implementations, the processor can be configured to adjust a position of the adjustable arm support and the at least one robotic arm in order to provide collision avoidance between the at least one robotic and surrounding objects.

Certain commanded robotic arm movements or positions may cause the arm to pass near or through a singularity. A singularity may refer to a pose at which the robot loses an effective degree of freedom, such as when two axes are aligned. In order to avoid such singularities, the processor may be configured to determine whether a commanded movement would result in or bring the robotic arm closer to a singularity and avoid the singularity via null space movement. In particular, the processor may be configured to adjust a position of the adjustable arm support and the robotic arm in order to avoid one or more singularities in the robotic arm.

In some implementations, the system may also be configured to move a plurality of links between different stages of a medical procedure. Certain medical procedures may involve different stages that occur in different regions of a patient. For example, a patient's abdomen may be divided into four regions or quadrants. Thus, the system may be configured to facilitate movement of a plurality of robotic arms between a first quadrant during a first stage of a procedure to a second quadrant during a second stage of a procedure. Thus, the system may be configured to move a first set of one or more links to perform a first stage of medical procedure using the medical tool in a first quadrant of a patient. The system can also move the first set links and a second set of one or more links in a null space such that a medical tool is able to access a second quadrant of the patient. The system may also be configured to move the first set of one or more links to perform a second stage of the medical procedure using the medical tool in the second quadrant of the patient. This movement in null space can allow the system to automatically move the link (e.g., robotic arms) such that the user is able to access different quadrants of a patient during different stages, without the cognitive load required for manually repositioning the links.

B. Null Space Movement Between Link Members and Patient Positioning Platform Using Shared Robotic DoFs.

In some implementations, the robotic system may further include a patient positioning platform that has at least one DoF. Another example of a robotic system 200 including a patient positioning platform 225 in accordance with aspects of this disclosure is illustrated in FIG. 22. The system 200 includes the patient positioning platform 225, a plurality of robotic arms 205, an adjustable arm support 210, and a set-up joint 215.

In the implementation illustrated in FIG. 22, the system 200 can provide shared robotic DoFs for null space movement between one or more DoFs associated with a first set of one or more motorized links (e.g., in the form of one or more robotic arms 205) in coordinated and/or synchronized movement with the one or more DoFs associated with a patient positioning platform 225 (e.g., in the form of a bed). For example, in come implementations, the patient positioning platform 225 can have three or more DoFs including vertical translation, lateral tilt, and Trendelenburg tilt. However, in other implementations, the patient positioning platform can have more or fewer than three DoFs.

As in the implementations above involving shared DoFs between a first set of links (e.g., of the robotic arms 205) and a second set of links (e.g., of set-up joints and an adjustable arm support 210), in the system 200 illustrated in FIG. 22, the system can maintain the pose of the ADMs of the robotic arms 205 and/or the remote centers of motion of any associated medical tools in place while the shared DoFs between the robotic arm(s) 205 and the patient positioning platform 225 provide null space movement.

From a systems standpoint, the overall system 200 can be partitioned into different robotic partitions. For example, the DoFs for patient positioning (e.g., those related to bed tilt, Trendelenburg, etc. of the patient positioning platform 225) can be viewed as one partition; the DoFs for the adjustable arm support 210 and set-up joint 215 can be viewed as another partition; and the DoFs for each of the robotic arms 205 can be viewed as a third partition. With this type of robot partitioning, the system 200 can include software that can lay the groundwork to exchange information between the various partitions. Each of these different robotic partitions can have its own set of kinematic chains and kinematic modes. In some implementations, sharing DoFs can involve sharing DoFs between two different types of kinematic modes. In an alternative implementation from partitioning shared DoFs into individual robotic partitions, the system 200 can include software that can also be configured to solve an entire kinematic chain of the overall system 200 (e.g., from the bed base of the patient positioning platform 225 to all of the robotic arms 205) in one set of equations, taking in all of the objectives, constraints, and/or user inputs in solving the set of equations.

Figure 27:
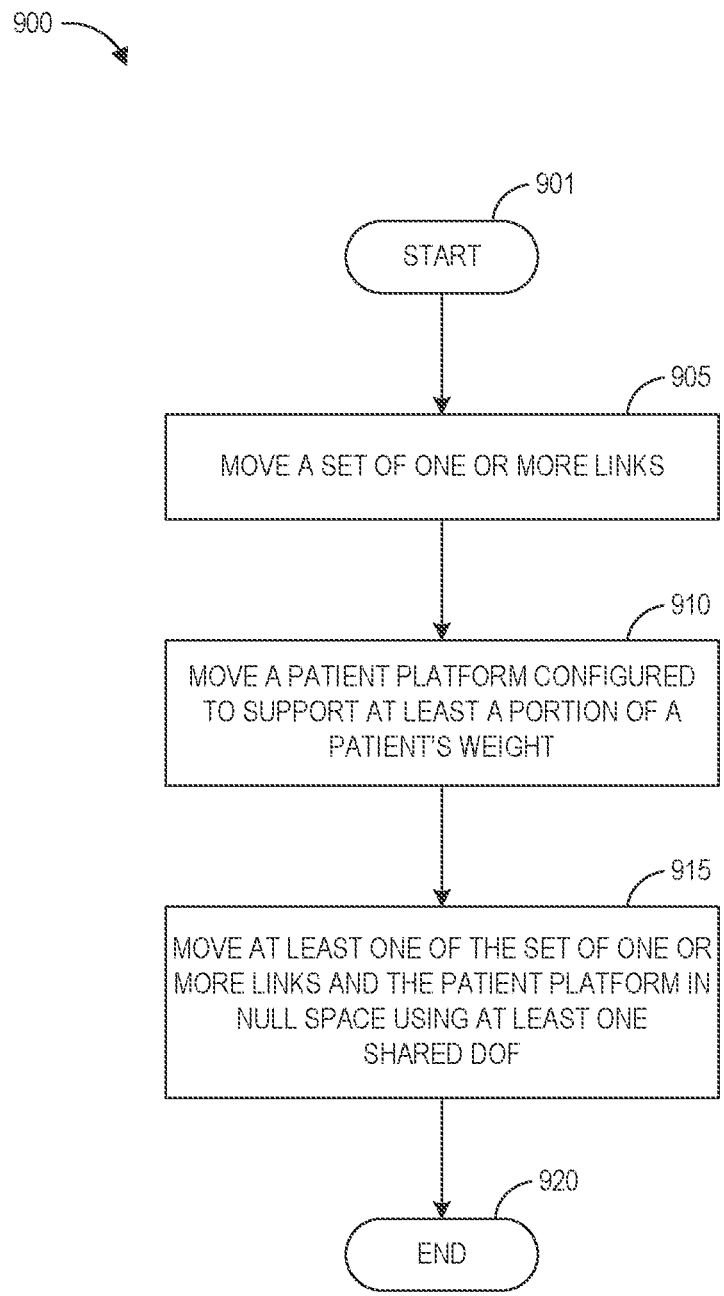
FIG. 27 is a flowchart illustrating yet another example method operable by a robotic system, or component(s) thereof, for null space movements between link members using shared robotic DoFs in accordance with aspects of this disclosure.

FIG. 27 is a flowchart illustrating yet another example method operable by a robotic system, or component(s) thereof, for null space movements between link members using shared robotic DoFs in accordance with aspects of this disclosure. For example, certain steps of method 900 illustrated in FIG. 27 may be performed by processor(s) and/or other component(s) of a medical robotic system (e.g., robotically-enabled system 10) or associated system(s). For convenience, the method 900 is described as performed by the "system" in connection with the description of the method 900.

The method 900 begins at block 901. At block 905, the system may move a set of one or more links. The first set of one or more links can have at least one DoF. In some implementations, the set of one or more links may form one or more robotic arms, an adjustable arm support, and/or a set-up joint. At block 910, the system may move a patient platform configured to support at least a portion of a patient's weight. The patient platform can have at least one DoF and the at least one DoF of each of the set of one or more links and the patient platform are shared. At block 915, the system may move at least one of the set of one or more links and the patient platform in null space using the shared at least one DoF. The method 900 ends at block 920.

In some implementations, the method 900 may further involve the system maintaining a position of an RCM of a medical tool coupled to the set of one or more links while moving the set of one or more links in at least one DoF. For example, the system may maintain the position of the RCM relative to the patient platform while moving the patient platform in at least one DoF. It may be desirable to maintain an RCM such that the medical tool does not apply unnecessary force to a body wall of a patient. Thus, maintaining the RCM with respect to the patient platform can be used reduce unnecessary forces applied to the patient's body wall.

3. Implementing Systems and Terminology

Implementations disclosed herein provide systems, methods and apparatus for kinematic optimization with shared robotic DoFs.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for kinematic optimization in shared robotic DoFs described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system, comprising:
   a patient platform;
   an adjustable arm support coupled to the patient platform for translating relative to the patient platform by moving the adjustable arm support;
   a plurality of links, each including a first end coupled to the adjustable arm support and a second end coupled to a base of the patient platform for raising or lowering the adjustable arm support relative to the patient platform;
   at least one robotic arm coupled to the adjustable arm support, the at least one robotic arm configured to be coupled to a medical tool that is configured to be delivered through an incision or natural orifice of a patient supported by the patient platform; and
   a processor configured to adjust a position of the adjustable arm support and the at least one robotic arm while maintaining a remote center of movement (RCM) of the medical tool.

2. The robotic medical system of claim 1, wherein the at least one robotic arm comprises at least two robotic arms.

3. The robotic medical system of claim 1, wherein the medical tool comprises an end effector that is inserted through the incision or natural orifice of the patient while maintaining the RCM.

4. The robotic medical system of claim 3, wherein the processor adjusts the position of the adjustable arm support and the at least one robotic arm while maintaining a position of the end effector of the medical tool coupled to the at least one robotic arm.

5. The robotic medical system of claim 3, wherein the processor adjusts the position of the adjustable arm support while the medical tool is teleoperatively controlled by a clinician.

6. The robotic medical system of claim 1, wherein the adjustable arm support has at least three degrees-of-freedom (DoFs).

7. The robotic medical system of claim 1, wherein the adjustable arm support has at least four DoFs.

8. The robotic medical system of claim 7, wherein the at least one robotic arm has at least six DoFs.

9. The robotic medical system of claim 1, wherein the processor is further configured to adjust the position of the adjustable arm support and the at least one robotic arm in order to provide collision avoidance between the at least one robotic arm and surrounding objects.

10. The robotic medical system of claim 1, wherein the processor is further configured to adjust the position of the adjustable arm support and the at least one robotic arm in order to avoid one or more singularities in the at least one robotic arm.

11. A method of adjusting a configuration of a surgical system, comprising:
    providing a medical platform comprising:
      a patient platform;
      an adjustable arm support coupled to the patient platform for translating relative to the patient platform by moving the adjustable arm support;
      a plurality of links, each including a first end coupled to the adjustable arm support and a second end coupled to a base of the patient platform for raising or lowering the adjustable arm support relative to the patient platform; and
      a pair of robotic arms coupled to the adjustable arm support, wherein each of the robotic arms is coupled to a respective medical tool; and
    adjusting a position of the adjustable arm support and each of the robotic arms coupled thereto via a processor of the surgical system while maintaining a remote center of movement (RCM) of each of the respective medical tools.

12. The method of claim 11, wherein the adjustable arm support is configured to move in at least three degrees of freedom.

13. The method of claim 12, wherein each of the robotic arms is configured to move in at least six degrees of freedom.

14. The method of claim 12, wherein the adjustable arm support is configured for vertical translation, horizontal translation, and tilt.

15. The method of claim 11, wherein the patient platform comprises an operating table, and wherein the RCM of each of the respective medical tools is maintained relative to the operating table.

16. The method of claim 15, wherein the operating table is configured to move in at least three degrees of freedom.

17. The method of claim 15, wherein the operating table is configured for lateral tilt, Trendelenburg tilt, and translation.

18. The method of claim 11, wherein each of the respective medical tools comprises an instrument or a camera.

19. The method of claim 11, wherein the adjustable arm support has a different number of degrees of freedom from each of the robotic arms.

20. The robotic medical system of claim 1, wherein:
    the plurality of links includes a first link and a second link; and
    the adjustable arm support is configured to rotate relative to the patient platform by moving the first end of the first link to a first height and moving the first end of the second link to a second height that is distinct from the first height.

* * * * *